United States Patent
Karasawa et al.

(10) Patent No.: US 12,059,579 B2
(45) Date of Patent: Aug. 13, 2024

(54) MEDICAL IMAGE PROCESSING DEVICE, TREATMENT SYSTEM, AND STORAGE MEDIUM

(71) Applicant: Toshiba Energy Systems & Solutions Corporation, Kawasaki (JP)

(72) Inventors: Kenichi Karasawa, Kawasaki (JP); Ryusuke Hirai, Shinagawa (JP); Tomoya Okazaki, Kawasaki (JP); Yasunori Taguchi, Kawasaki (JP); Keiko Okaya, Setagaya (JP); Shinichiro Mori, Chiba (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 997 days.

(21) Appl. No.: 16/979,619

(22) PCT Filed: Mar. 7, 2019

(86) PCT No.: PCT/JP2019/009137
§ 371 (c)(1),
(2) Date: Sep. 10, 2020

(87) PCT Pub. No.: WO2019/181542
PCT Pub. Date: Sep. 26, 2019

(65) Prior Publication Data
US 2021/0038917 A1    Feb. 11, 2021

(30) Foreign Application Priority Data
Mar. 20, 2018    (JP) .................. 2018-053470

(51) Int. Cl.
*A61N 5/10* (2006.01)
*A61B 6/00* (2024.01)
(Continued)

(52) U.S. Cl.
CPC ............ *A61N 5/1049* (2013.01); *A61B 6/463* (2013.01); *A61B 6/487* (2013.01); *A61N 5/1037* (2013.01);
(Continued)

(58) Field of Classification Search
CPC ............... A61N 5/1049; A61N 5/1037; A61N 2005/1056; A61N 2005/1062;
(Continued)

(56) References Cited

U.S. PATENT DOCUMENTS

2005/0276377 A1 * 12/2005 Carol .................. A61N 5/1037
378/65
2015/0254859 A1 * 9/2015 Parikh ...................... G06T 7/74
382/103
(Continued)

FOREIGN PATENT DOCUMENTS

CN  104587609  *  5/2015
JP  2012-30005 A  2/2012
(Continued)

OTHER PUBLICATIONS

International Search Report issued on Jun. 4, 2019 in PCT/JP2019/009137 filed on Mar. 7, 2019, 1 page.

*Primary Examiner* — Alexei Bykhovski
(74) *Attorney, Agent, or Firm* — Oblon, McClelland, Maier & Neustadt, L.L.P.

(57) ABSTRACT

A medical image processing device includes a region-of-interest acquirer, a treatment plan acquirer, a degree-of-influence calculator, and a display controller. The region-of-interest acquirer is configured to acquire a partial region within a body of a patient as a region of interest. The treatment plan acquirer is configured to acquire treatment plan information determined in a planning stage of radiation treatment to be performed on the patient. The degree-of-
(Continued)

influence calculator is configured to calculate a degree of influence representing an influence on the region of interest up to a range until radiation with which the patient is irradiated reaches a target portion to be treated within the body of the patient. The display controller is configured to generate a display image in which information regarding the degree of influence is superimposed on a current fluoroscopic image of the patient and causes a display to display the display image.

16 Claims, 9 Drawing Sheets

(51) Int. Cl.
| | |
|---|---|
| *A61B 6/46* | (2024.01) |
| *G06F 3/14* | (2006.01) |
| *G06K 9/32* | (2006.01) |
| *G06T 7/00* | (2017.01) |
| *G06T 7/70* | (2017.01) |
| *G06T 11/00* | (2006.01) |

(52) U.S. Cl.
CPC ............. *G06F 3/14* (2013.01); *G06T 7/0012* (2013.01); *G06T 7/70* (2017.01); *G06T 11/003* (2013.01); *G06T 2207/10064* (2013.01); *G06T 2207/10081* (2013.01); *G06T 2207/10124* (2013.01); *G06T 2207/30096* (2013.01)

(58) Field of Classification Search
CPC ........ A61N 5/1039; A61N 5/10; A61B 6/463; A61B 6/487; A61B 6/5294; A61B 6/032; A61B 6/5229; G06F 3/14; G06F 3/147; G06T 7/0012; G06T 7/70; G06T 11/003; G06T 2207/10064; G06T 2207/10081; G06T 2207/10124; G06T 2207/30096; G09G 2380/08; G09G 2340/12

See application file for complete search history.

(56) References Cited

U.S. PATENT DOCUMENTS

| | | | |
|---|---|---|---|
| 2016/0148399 A1* | 5/2016 | Kim | G06T 7/0012 |
| | | | 382/131 |
| 2016/0213948 A1* | 7/2016 | Renne | A61N 5/1039 |
| 2018/0056091 A1* | 3/2018 | Jordan | A61N 5/107 |
| 2018/0193672 A1 | 7/2018 | Hirai et al. | |
| 2019/0059841 A1* | 2/2019 | Palma | A61B 6/032 |

FOREIGN PATENT DOCUMENTS

| | | | |
|---|---|---|---|
| JP | 2016059580 | * | 4/2016 |
| JP | 2018-29852 A | | 3/2018 |
| KR | 10-2012-0087862 A | | 8/2012 |
| WO | WO 2012/088321 A1 | | 6/2012 |

* cited by examiner

MEDICAL IMAGE PROCESSING DEVICE, TREATMENT SYSTEM, AND STORAGE MEDIUM

TECHNICAL FIELD

Embodiments of the present invention relate to a medical image processing device, a treatment system, and a medical image processing program.

Priority is claimed on Japanese Patent Application No. 2018-053470, filed Mar. 20, 2018, the content of which is incorporated herein by reference.

BACKGROUND ART

Radiation treatment is a treatment method of irradiating a lesion within a patient's body with radiation to destroy the lesion. At this time, the radiation is required to be accurately radiated to the position of the lesion. This is because, when normal tissue within the patient's body is irradiated with the radiation, the normal tissue may be affected. Thus, when the radiation treatment is performed, computed tomography (CT) is first performed in advance in a treatment planning stage and the position of the lesion within the patient's body is three-dimensionally ascertained. The radiation irradiation direction and a radiation irradiation intensity are planned to reduce irradiation for the normal tissue on the basis of the ascertained position of the lesion. Thereafter, the position of the patient in a treatment stage is aligned with the position of the patient planned in the treatment planning stage and a lesion is irradiated with radiation in accordance with the irradiation direction or the irradiation intensity planned in the treatment planning stage.

In the position alignment of the patient in the treatment stage, image collation between a fluoroscopic image of the inside of the patient's body captured in a state in which the patient is laid on the bed immediately before the start of treatment and a digitally reconstructed radiograph (DRR) image in which the fluoroscopic image is virtually reconstructed from a three-dimensional CT image captured at the time of the treatment planning is performed and position deviation of the patient between images is obtained. The bed is moved on the basis of the obtained position deviation of the patient. Thereby, the position of a lesion, bone, or the like within the patient's body is aligned with that planned in the treatment planning.

The position deviation of the patient is obtained by seeking a position in the CT image so that the DRR image most similar to the fluoroscopic image is reconstructed. Many methods of automatically seeking the position of a patient using a computer have been proposed. However, a user (a doctor or the like) finally confirms an automated seeking result by comparing the fluoroscopic image with the DRR image. As soon as the confirmation by the user (the doctor or the like) is obtained, the irradiation with radiation is performed. In radiation treatment, such patient positioning work is performed every time before the treatment is started.

Also, the patient's posture should not change while the radiation treatment is being performed together with the patient positioning work. Thus, the patient is fixed with a fixing tool or the like so that the patient cannot move while the radiation treatment is being performed. Incidentally, the patient positioning work is work in which a required time period significantly differs according to the skill of the user (the doctor or the like). However, the patient positioning work is not easy because the patient's condition changes between a treatment planning stage and a treatment stage. If the time period required for the patient positioning work becomes long, there is a problem that the burden on the patient will increase and the accuracy of patient positioning that has been performed will deteriorate.

Thus, for example, technology disclosed in Patent Document 1 has been proposed as technology for facilitating the patient positioning work. In the technology disclosed in Patent Document 1, the user (the doctor or the like) can easily confirm a current position of the patient when an amount of deviation between the patient shown in a CT image captured in a treatment planning stage and the patient shown in a fluoroscopic image captured in the treatment stage is shown. More specifically, in the technology disclosed in Patent Document 1, a luminance gradient of each pixel included in the CT image captured in the treatment planning stage and a luminance gradient of each pixel included in the fluoroscopic image captured in the treatment stage are calculated. Thereby, it is possible to determine a boundary portion (particularly, a bone portion) of the patient who is an object shown in each image in the technology disclosed in Patent Document 1. In the technology disclosed in Patent Document 1, boundary portion deviation (an amount of boundary portion deviation) of the object is calculated on the basis of the luminance gradient calculated from each image and the image representing the calculated deviation is superimposed and displayed on the fluoroscopic image. In other words, in the technology disclosed in Patent Document 1, position deviation of the patient of the treatment stage (at present) with respect to the treatment planning stage is presented to the user (the doctor or the like) by obtaining bone portion deviation of the patient and superimposing and displaying an image in which the bone portion deviation is highlighted on the fluoroscopic image.

However, the portion of the patient's bone is not necessarily in the same state in the treatment planning stage and the treatment stage. For example, when there is a joint or the like in the vicinity of a portion where the radiation treatment is performed, the bone portion of the patient does not necessarily coincide between the treatment planning stage and the treatment stage according to the posture of the patient. Moreover, a position of a target lesion which is irradiated with radiation within the patient's body is not necessarily in the vicinity of a bone. Thus, in the patient positioning based on the bone portion deviation of the patient as in the technology disclosed in Patent Document 1, the patient positioning work may not be easy.

Also, although it is important that the lesion be irradiated with a dose of radiation planned in the treatment planning stage in radiation treatment, a distribution of the dose of radiation with which the lesion is irradiated changes with the composition of tissues within the patient's body through which the radiation passes. For example, a case in which there is a region of air such as intestinal gas, which was not present in the treatment planning stage, on a path through which radiation passes is conceivable. This region of air is likely to affect the dose of radiation radiated to the lesion. However, in the technology disclosed in Patent Document 1, no consideration is given to a path along which the radiation that is radiated passes through the patient's body.

Thus, even if the technology disclosed in Patent Document 1 is used, it is still necessary for the user (the doctor or the like) to visually confirm a result of the patient positioning work. Also, because a radiation irradiation direction in radiation treatment is not always limited to a certain direction such as, for example, a horizontal direction or a vertical direction, it is necessary to take into account a radiation irradiation direction when the user (the doctor or the like) visually confirms the result of the patient positioning work.

CITATION LIST

Patent Literature

[Patent Document 1]
Japanese Unexamined Patent Application, First Publication No. 2012-030005

SUMMARY OF INVENTION

Technical Problem

An objective of an aspect of the present invention is to provide a medical image processing device, a treatment system, and a medical image processing program for enabling a position of a patient to be easily confirmed in patient position alignment work to be performed before radiation treatment is started.

Solution to Problem

A medical image processing device according to an aspect of the present embodiment includes a region-of-interest acquirer, a treatment plan acquirer, a degree-of-influence calculator, and a display controller. The region-of-interest acquirer is configured to acquire a partial region within a body of a patient as a region of interest. The treatment plan acquirer is configured to acquire treatment plan information determined in a planning stage of radiation treatment to be performed on the patient. The degree-of-influence calculator is configured to calculate a degree of influence representing an influence on the region of interest up to a range until radiation with which the patient is irradiated reaches a target portion to be treated within the body of the patient. The display controller is configured to generate a display image in which information regarding the degree of influence is superimposed on a current fluoroscopic image of the patient and causes a display to display the display image.

Advantageous Effects of Invention

According to the above-described aspect, it is possible to provide a medical image processing device, a treatment system, and a medical image processing program for enabling a position of a patient to be easily confirmed in patient position alignment work to be performed before radiation treatment is started.

DESCRIPTION OF EMBODIMENTS

Hereinafter, a medical image processing device, a treatment system, and a medical image processing program of embodiments will be described with reference to the drawings.

First Embodiment

Figure 1:
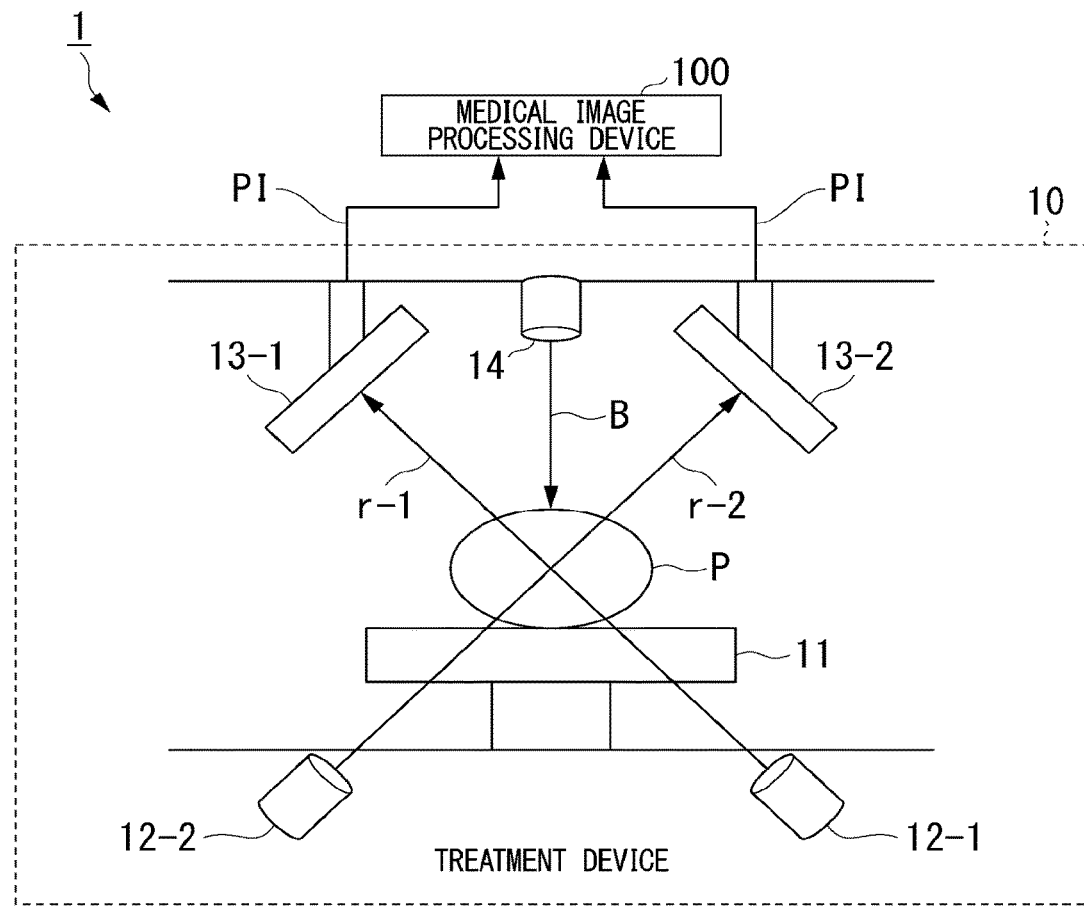
FIG. 1 is a block diagram showing a schematic configuration of a treatment system including a medical image processing device of a first embodiment.

FIG. 1 is a block diagram showing a schematic configuration of a treatment system including a medical image processing device of a first embodiment. A treatment system 1 shown in FIG. 1 includes a medical image processing device 100 and a treatment device 10.

First, the treatment device 10 constituting the treatment system 1 will be described. The treatment device 10 includes a treatment table 11, two radiation sources 12 (a radiation source 12-1 and a radiation source 12-2), two radiation detectors 13 (a radiation detector 13-1 and a radiation detector 13-2), and a treatment beam irradiation gate 14.

Also, a hyphen "-" indicated after a reference numeral shown in FIG. 1 and a number subsequent to the hyphen are used for identifying an associated relationship. For example, in the associated relationship between the radiation source 12 and the radiation detector 13 in the treatment device 10, a state in which the radiation source 12-1 and the radiation detector 13-1 correspond to each other to form one set is shown and a state in which the radiation source 12-2 and the radiation detector 13-2 correspond to each other to form another set is shown. That is, in the following description, the hyphen "-" indicated after each reference numeral and a number subsequent to the hyphen represent that components of the same set correspond to each other. In the following description, when a plurality of identical components are represented without being distinguished, they are represented without the hyphen "-" and the number subsequent to the hyphen.

The treatment table 11 is a bed on which a subject (a patient) P which will undergo radiation treatment is fixed.

The radiation source 12-1 radiates radiation r-1 for seeing through the body of the patient P at a predetermined angle. The radiation source 12-2 radiates radiation r-2 for seeing through the body of the patient P at a predetermined angle different from that of the radiation source 12-1. The radiation r-1 and the radiation r-2 are, for example, X-rays. In FIG. 1, a case in which X-ray photography is performed in two directions on the patient P fixed on the treatment table 11 is shown. Also, the illustration of a controller that controls the irradiation with the radiation r by the radiation source 12 is omitted from FIG. 1.

The radiation detector 13-1 detects the radiation r-1 which has been radiated from the radiation source 12-1 and has arrived at the radiation detector 13-1 after passing through the inside of the body of the patient P and generates a fluoroscopic image PI of the inside of the body of the patient P according to a magnitude of energy of the detected radiation r-1. The radiation detector 13-2 detects the radiation r-2 which has been radiated from the radiation source 12-2 and has arrived at the radiation detector 13-2 after passing through the inside of the body of the patient P and generates a fluoroscopic image PI of the inside of the body of the patient P according to a magnitude of energy of the detected radiation r-2. The radiation detectors 13 are detectors arranged in a two-dimensional array shape and generate a digital image in which a magnitude of energy of the radiation r arriving at each detector is represented by a digital value as a fluoroscopic image PI. The radiation detector 13 is, for example, a flat panel detector (FPD), an image intensifier, or a color image intensifier. The radiation detector 13 outputs the generated fluoroscopic image PI to the medical image processing device 100. Also, the illustration of a controller that controls the generation of the fluoroscopic image PI by the radiation detector 13 is omitted from FIG. 1.

In the treatment device 10, a set of a radiation source 12 and a radiation detector 13 constitutes an imaging device in the treatment system 1.

Also, in FIG. 1, a configuration of the treatment device 10 including two sets of radiation sources 12 and radiation detectors 13, i.e., two imaging devices, is shown. However, the number of imaging devices provided in the treatment device 10 is not limited to a configuration including two imaging devices as shown in FIG. 1, i.e., a configuration including two sets of the radiation sources 12 and the radiation detectors 13. For example, the treatment device 10 may be configured to include three or more imaging devices (three or more sets of radiation sources 12 and radiation detectors 13). Also, the treatment device 10 may be configured to include one imaging device (a set of a radiation source 12 and a radiation detector 13).

The treatment beam irradiation gate 14 radiates radiation as a treatment beam B for destroying a lesion, which is a target portion to be treated within the body of the patient P. The treatment beam B is, for example, X-rays, γ-rays, an electron beam, a proton beam, a neutron beam, a heavy particle beam, or the like. Also, the illustration of a controller that controls the irradiation with the treatment beam B by the treatment beam irradiation gate 14 is omitted from FIG. 1.

Also, in FIG. 1, the configuration of the treatment device 10 including one treatment beam irradiation gate 14 that is fixed is shown. However, the treatment device 10 is not limited to the configuration including only one treatment beam irradiation gate 14 and may include a plurality of treatment beam irradiation gates. For example, although the configuration of the treatment device 10 including the treatment beam irradiation gate 14 for irradiating the patient P with the treatment beam B in a vertical direction is shown in FIG. 1, the treatment system 1 may further include a treatment beam irradiation gate for irradiating the patient P with the treatment beam in a horizontal direction. For example, although the configuration of the treatment device 10 including the treatment beam irradiation gate 14 fixed at a position where the patient P is irradiated with the treatment beam B in a vertical direction is shown in FIG. 1, the treatment beam irradiation gate 14 provided in the treatment system 1 may include a treatment beam irradiation gate configured to irradiate the patient P with treatment beams in various directions (at various angles) by moving the treatment beam irradiation gate so that the treatment beam irradiation gate rotates around the patient P.

The medical image processing device 100 controls a process of irradiating the lesion within the body of the patient P to be treated in the radiation treatment with the treatment beam B on the basis of fluoroscopic images PI output from the radiation detector 13-1 and the radiation detector 13-2. At this time, the medical image processing device 100 tracks an organ, which moves due to the motion of respiration or heartbeat of the patient P, such as the lung or the liver and causes the treatment beam irradiation gate 14 to irradiate the lesion within the body of the patient P with the treatment beam B at an appropriate timing. Also, tracking of a lesion in the medical image processing device 100 is performed on the basis of an image (a three-dimensional computed tomography (CT) image or a fluoroscopic image PI) of the patient P captured before the radiation treatment is performed in a stage such as the treatment planning stage and a current fluoroscopic image PI of the patient P.

Also, the medical image processing device 100 presents information regarding the position of the patient P to be confirmed in the patient positioning work performed by a radiation treatment provider (a doctor or the like) using the treatment system 1 before the treatment is started. At this time, the medical image processing device 100 sequentially detects deviations between current positions of the patient P laid on the treatment table 11 and positions of the patient P planned at the time of the treatment planning on the basis of an image (a CT image or a fluoroscopic image PI) of the patient P captured in the treatment planning stage and a current fluoroscopic image PI of the patient P. The medical image processing device 100 sequentially presents information representing the detected position deviations of the patient P to the radiation treatment provider (the doctor or the like) using the treatment system 1.

Also, the medical image processing device 100 and the radiation detector 13 provided in the treatment device 10 may be connected by a local region network (LAN) or a wide region network (WAN).

Here, the treatment planning that is performed before the radiation treatment is performed will be described. Before the treatment, a treatment plan for determining energy of a treatment beam B (radiation) with which the patient P is irradiated, an irradiation direction, a shape of an irradiation range, a distribution of a dose when the treatment beam B is radiated a plurality of times, and the like is made in the treatment planning. More specifically, a treatment planner (a doctor or the like) first designates a boundary between a tumor (lesion) region and a normal tissue region, a boundary between a tumor and an important organ around the tumor, or the like with respect to a CT image captured in the treatment planning stage. In the treatment planning, a direction (a path) or an intensity of the treatment beam B to be radiated is determined on the basis of a depth from a body surface of the patient P to a position of the tumor or a size of the tumor calculated from information about the designated tumor.

The designation of the boundary between the tumor region and the normal tissue region described above corresponds to designation of a position and a volume of the tumor. The volume of this tumor is referred to as a gross tumor volume (GTV), a clinical target volume (CTV), an internal target volume (ITV), a planning target volume (PTV), or the like. The GTV is a volume of the tumor capable of being visually confirmed from the image and is a volume required to be irradiated with a sufficient dose of the treatment beam B in radiation treatment. The CTV is a volume including the GTV and a latent tumor to be treated. The ITV is a volume obtained by adding a predetermined margin to the CTV in consideration of the movement of the CTV due to predicted physiological movement of the patient P and the like. The PTV is a volume obtained by adding a margin to the ITV in consideration of an error in alignment of the patient P performed when treatment is performed. The relationship of the following Expression (1) is established between these volumes.

[Math. 1]

$$GTV \subseteq CYV \subseteq ITV \subseteq PYV \qquad (1)$$

Thus, in the treatment planning stage, a position and a range (a region) where the patient P is irradiated with the treatment beam B are determined by adding a margin in consideration of the error that is likely to occur in the actual treatment. For example, the error that is likely to occur in the actual treatment considered at this time is position deviation of the patient P, which is likely to occur in the patient positioning work to be performed so that a position of a lesion or bone within the body of the patient P is aligned with a position planned at the time of the treatment planning, or the like.

Thus, the radiation treatment provider (the doctor or the like) using the treatment system 1 performs the patient positioning work so that an error, which is likely to occur in the actual treatment, is reduced while visually confirming information regarding position deviations of the patient P which are sequentially presented from the medical image processing device 100.

Figure 2:
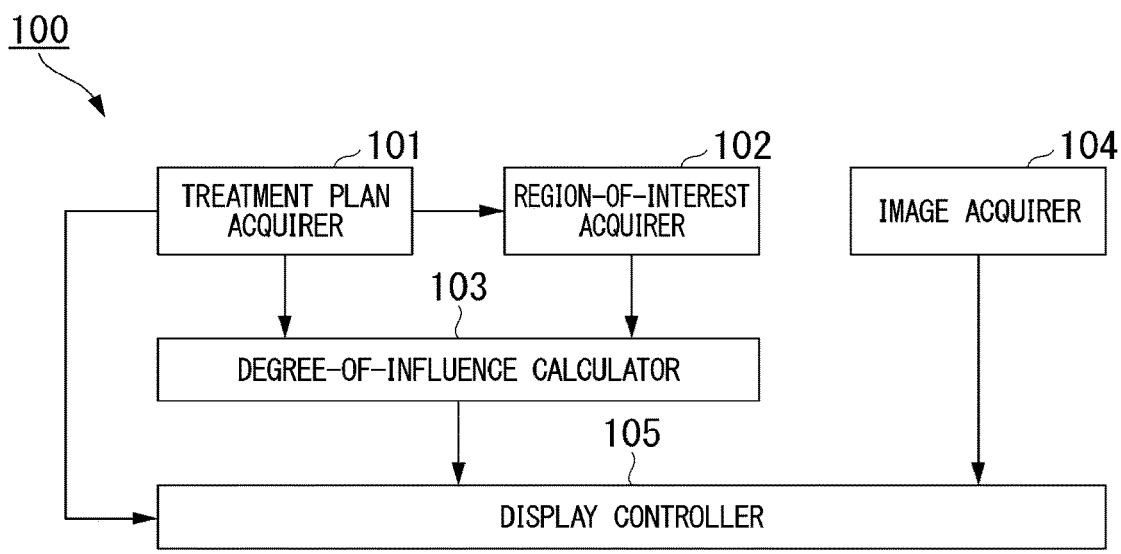
FIG. 2 is a block diagram showing a schematic configuration of the medical image processing device of the first embodiment.

Next, a configuration of the medical image processing device 100 constituting the treatment system 1 will be described. FIG. 2 is a block diagram showing a schematic configuration of the medical image processing device 100 of the first embodiment. Also, only a configuration related to a function of presenting information representing position deviation of the patient P which is confirmed by the radiation treatment provider (the doctor or the like) using the treatment system 1 when the patient positioning work is performed is shown in FIG. 2. The medical image processing device 100 shown in FIG. 2 includes a treatment plan acquirer 101, a region-of-interest acquirer 102, a degree-of-influence calculator 103, an image acquirer 104, and a display controller 105 as components for implementing a function of presenting information representing position deviation of the patient P.

The treatment plan acquirer 101 acquires information regarding a treatment plan made in the treatment planning stage (hereinafter referred to as "treatment plan information"). Here, the treatment plan information is information including a direction (a path) and an intensity of the treatment beam B to be radiated in the treatment, a range (a region) to be irradiated with the treatment beam B, a so-called irradiation field, a position of a tumor (a lesion) within the body of the patient P (i.e., a position where the treatment beam B is radiated), a size of the tumor (the lesion), and the like. The treatment plan acquirer 101 outputs the acquired treatment plan information to each of the region-of-interest acquirer 102 and the degree-of-influence calculator 103. Also, the treatment plan acquirer 101 acquires the CT image used in the treatment plan. The treatment plan acquirer 101 outputs the acquired CT image to each of the region-of-interest acquirer 102, the degree-of-influence calculator 103, and the display controller 105.

The region-of-interest acquirer 102 acquires (extracts) a region of interest (ROI) when radiation treatment is performed on the patient P on the basis of treatment plan information output from the treatment plan acquirer 101. Here, the region of interest ROI is a partial region within the body of the patient P which is likely to have an influence on the effect of radiation treatment to be performed on the tumor (the lesion) within the body of the patient P shown in the CT image output from the treatment plan acquirer 101. Accordingly, the region of interest ROI is a region where the position of the patient P is required to be aligned with the position planned in the treatment planning stage before the radiation treatment is started, i.e., a region important for irradiating the lesion with the treatment beam B in the radiation treatment. The region-of-interest acquirer 102 outputs information representing each acquired (extracted) region of interest ROI (hereinafter referred to as "ROI information") to the degree-of-influence calculator 103.

The degree-of-influence calculator 103 calculates the degree of influence representing a level of an influence of the treatment beam B to be radiated to the lesion within the body of the patient P on each region of interest ROI represented by the ROI information output from the region-of-interest acquirer 102 on the basis of the treatment plan information output from the treatment plan acquirer 101. At this time, the degree-of-influence calculator 103 calculates the degree of influence on the basis of a positional relationship between an irradiation path of the treatment beam B (radiation) and a position of each pixel included in the region of interest ROI. Here, the degree of influence calculated by the degree-of-influence calculator 103 represents that, when the degree of influence is higher, deviation between the position of the patient P planned in the treatment planning stage and a current position of the patient P is more likely to have an influence on the effect of radiation treatment. Also, the degree-of-influence calculator 103 calculates a degree of influence of the treatment beam B with respect to a position of each pixel included in the region of interest ROI up to a range that is a reachable distance of the treatment beam B. This is because the energy of the treatment beam B is lost due to a process in which the lesion is irradiated with the treatment beam B and it is not necessary to calculate the degree of influence on the treatment beam B that passes through the lesion. The degree-of-influence calculator 103 outputs information regarding each degree of influence calculated with respect to the position of each pixel included in the region of interest ROI to the display controller 105.

The image acquirer 104 acquires fluoroscopic images PI of the patient P captured during the patient positioning work. Here, the fluoroscopic images PI are images of the inside of the body of the patient P captured at predetermined time intervals in a state in which the patient P is laid on the treatment table 11 in the patient positioning work. That is, the fluoroscopic image PI is a fluoroscopic image PI generated by the radiation detector 13 detecting radiation r radiated from the radiation source 12 and passing through the body of the patient P at the time of the patient positioning work. Also, the image acquirer 104 may include an interface for connecting to the radiation detector 13 provided in the treatment device 10. The image acquirer 104 outputs the acquired fluoroscopic image PI to the display controller 105.

Also, the image acquirer 104 may acquire a CT image used in the treatment plan instead of the treatment plan acquirer 101. In this case, the image acquirer 104 outputs the acquired CT image to each of the region-of-interest acquirer 102, the degree-of-influence calculator 103, and the display controller 105 instead of the treatment plan acquirer 101.

The display controller 105 generates a display image in which information regarding the degree of influence output from the degree-of-influence calculator 103 is superimposed on the fluoroscopic image PI output from the image acquirer 104. Here, the display image generated by the display controller 105 is an image in which pixels of a location where there is deviation between the position of the patient P shown in the CT image output from the treatment plan acquirer 101 and the position of the patient P shown in the fluoroscopic image PI output from the image acquirer 104 are highlighted (conspicuous) in accordance with the associated information regarding the degree of influence. For example, the display controller 105 generates a display image in which a portion to be highlighted is conspicuous by differentiating colors of pixels of a location where the position of the patient P deviates in accordance with a magnitude of the degree of influence. The display controller 105 outputs the generated display image to a display device (not shown) such as a liquid crystal display (LCD), thereby causing the display device to display the display image.

Also, the display device (not shown) may be configured to be provided in the medical image processing device 100 or may be configured to be provided outside the medical image processing device 100. Also, the display device (not shown) may be configured to be provided in the treatment device 10.

According to this configuration, the medical image processing device 100 sequentially detects position deviations of the patient P in consideration of the irradiation path of the treatment beam B important in the patient positioning work to be performed before the treatment is started. The medical image processing device 100 sequentially presents display images to the radiation treatment provider (the doctor or the like) using the treatment system 1 by causing the display device (not shown) to display the display images visually representing information regarding the sequentially detected position deviations of the patient P. Thereby, the radiation treatment provider (the doctor or the like) using the treatment system 1 can perform the patient positioning work while visually confirming information regarding position deviations of the patient P sequentially presented from the medical image processing device 100.

Also, some of the functional units provided in the medical image processing device 100 described above may be software function units that function by a processor, for example, such as a central processing unit (CPU) or a graphics processing unit (GPU), executing a program stored in a storage device. Here, the storage device may be implemented by a read only memory (ROM), a random-access memory (RAM), a hard disk drive (HDD), a flash memory, or the like. The program executed by the processor such as a CPU or a GPU may be pre-stored in the storage device of the medical image processing device 100 or may be downloaded from another computer device via a network. Also, the program stored in the portable storage device may be installed in the medical image processing device 100. Also, some or all of the functional units provided in the above-described medical image processing device 100 may be hardware function units based on a field programmable gate array (FPGA), a large-scale integration (LSI) circuit, an application specific integrated circuit (ASIC), and the like.

Figure 3:
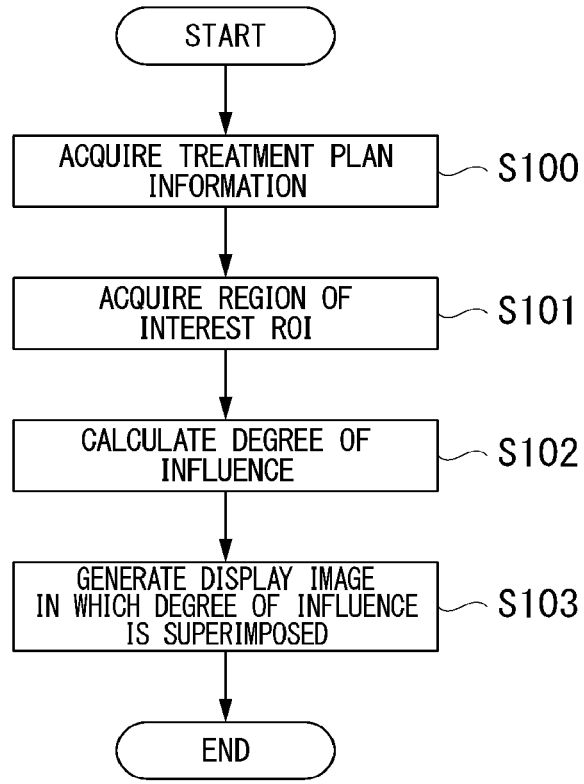
FIG. 3 is a flowchart showing a flow of an operation of the medical image processing device of the first embodiment.

Here, the operation of the medical image processing device 100 constituting the treatment system 1 will be schematically described. In the following description, an operation in which the medical image processing device 100 presents information regarding position deviation of the patient P to the radiation treatment provider (the doctor or the like) using the treatment system 1 for performing patient positioning work will be schematically described. FIG. 3 is an example of a flowchart showing a flow of an operation of presenting information regarding position deviation of the patient P in the medical image processing device 100 of the first embodiment.

When the medical image processing device 100 starts an operation in the patient positioning work to be performed before treatment is started, the treatment plan acquirer 101 first acquires treatment plan information (step S100). Subsequently, the region-of-interest acquirer 102 acquires a region of interest ROI on the basis of the treatment plan information output from the treatment plan acquirer 101 (step S101). Subsequently, the degree-of-influence calculator 103 calculates a degree of influences on each region of interest ROI represented by the ROI information output from the region-of-interest acquirer 102 on the basis of the treatment plan information output from the treatment plan acquirer 101 (step S102). Subsequently, the display controller 105 generates a display image in which information regarding the degree of influence output from the degree-of-influence calculator 103 is superimposed on the fluoroscopic image PI output from the image acquirer 104 (step S103).

Next, the operation of each component provided in the medical image processing device 100 constituting the treatment system 1 will be described in detail. First, a method of acquiring a region of interest ROI in the region-of-interest acquirer 102 constituting the medical image processing device 100 will be described.

The region-of-interest acquirer 102 acquires (extracts) the region of interest ROI on the basis of the treatment plan information output from the treatment plan acquirer 101 as described above. At this time, the region-of-interest acquirer 102 acquires (extracts) the region of interest ROI included within a region around an irradiation path of the treatment beam B (radiation) with which a lesion within the body of the patient P is irradiated. For example, when the number of irradiation paths of the treatment beam B to be radiated in the radiation treatment is one, the region-of-interest acquirer 102 acquires (extracts) the region of interest ROI including at least an irradiation path of one treatment beam B. Also, for example, when so-called scanning irradiation in which the treatment beam B is radiated to scan the entire region of the lesion in the radiation treatment is performed, the region-of-interest acquirer 102 acquires (extracts) the region of interest ROI including at least a region of a range (a width) in which irradiation paths of a plurality of treatment beams B for performing scanning irradiation are combined. Also, the region-of-interest acquirer 102 may acquire (extract) a region of interest ROI including at least a region where a predetermined range (width) is further provided around the range (width) of the irradiation path of the treatment beam B. The range (the width) to be further provided around the range (the width) of the irradiation path of the treatment beam B may be set by the treatment planner or the radiation treatment provider (the doctor or the like). In this case, the radiation treatment provider (the doctor or the like) using the treatment system 1 is required to perform position alignment of the patient P with respect to a wider range in the patient positioning work, so that it is possible to more strictly align the position of the patient P, in other words, it is possible to make a result of performing the patient positioning work with a margin.

Also, a plurality of methods can be considered for the method of acquiring the region of interest ROI in the region-of-interest acquirer 102.

A first method of acquiring a region of interest ROI is a method of acquiring a location having a large image difference, i.e., a location where deviation of the patient P is large, as the region of interest ROI by calculating a difference between a digitally reconstructed radiograph (DRR) image in which a fluoroscopic image PI is virtually reconstructed from a three-dimensional CT image or the fluoroscopic image PI captured at the time of the treatment planning and a current fluoroscopic image PI of the patient P. Also, in this method, the region-of-interest acquirer 102 also uses the current fluoroscopic image PI of the patient P acquired by the image acquirer 104 to acquire the region of interest ROI. Thus, the region-of-interest acquirer 102 acquires the current fluoroscopic image PI of the patient P from the image acquirer 104.

In the first method of acquiring a region of interest ROI, the region-of-interest acquirer 102 reconstructs a DRR image of a direction (an orientation) which is the same as that of the patient P shown in the fluoroscopic image PI output from the image acquirer 104 from the CT image output from the treatment plan acquirer 101. The region-of-interest acquirer 102 collates the position of the patient P shown in the fluoroscopic image PI output from the image acquirer 104 with the position of the patient P shown in the reconstructed DRR image and detects position deviation between a current position of the patient P and the position of the patient P planned at the time of the treatment planning. The region-of-interest acquirer 102 acquires a location where the detected position deviation of the patient P is large as the region of interest ROI. More specifically, the region-of-interest acquirer 102 calculates a difference between a luminance gradient of each pixel included in the fluoroscopic image PI and a luminance gradient of each pixel included in the DRR image and acquires pixels having calculated luminance gradient differences greater than a predetermined difference threshold value as the region of interest ROI. Thereby, for example, the region-of-interest acquirer 102 can acquire a location where a contour portion such as a lesion or bone within the body of the patient P has large deviation as the region of interest ROI. Also, the region-of-interest acquirer 102 may divide a region of each of the fluoroscopic image PI and the DRR image into regions, each of which has a predetermined size, calculate luminance gradient differences in units of the regions obtained through the division, and acquire a region having a calculated luminance gradient difference greater than the predetermined difference threshold value as the region of interest ROI.

Also, in the fluoroscopic image PI and the DRR image, a large difference from the original pixel values may be considered due to, for example, a brightness difference of the entire image, even if values of pixels (pixel values) of the same location are provided. Thus, the region-of-interest acquirer 102 may calculate a luminance gradient difference between the pixels in a state in which degrees of similarity of the pixel values of the pixels are similar using, for example, normalized cross-correlation or the like.

Also, a second method of acquiring a region of interest ROI is a method in which the treatment planner or the radiation treatment provider (the doctor or the like) sets the region of interest ROI with respect to a CT image, a DRR image, and a fluoroscopic image PI captured in the treatment planning stage. In this case, the treatment planner or the radiation treatment provider (the doctor or the like) confirms an image for setting the region of interest ROI and inputs (sets) a location where deviation is large, a location where an important organ is present, or a region of a contour portion thereof as a location or a region where the position of the patient P is required to be aligned with a position planned in the treatment planning stage in the patient positioning work. Also, the input (setting) of a location or a region where the position of the patient P is required to be aligned with a position planned in the treatment planning stage may be changed or added to while the radiation treatment provider (the doctor or the like) is performing the patient positioning work. The region-of-interest acquirer 102 acquires a location set by the treatment planner or the radiation treatment provider (the doctor or the like) as the region of interest ROI.

Also, the treatment planner or the radiation treatment provider (the doctor or the like) may also input (set) a location where deviation is large, a location where an important organ is present, or a region of a contour portion thereof with respect to a DRR image or a fluoroscopic image PI if a location where deviation is large, a location where an important organ is present, or a region of a contour portion thereof may be input (set) with respect to a CT image. Thus, the region-of-interest acquirer 102 may represent the acquired region of interest ROI by coordinates of a three-dimensional space representing a position of each pixel included in the CT image or may represent the acquired region of interest ROI by coordinates of a two-dimensional space representing a position of each pixel included in the DRR image, the fluoroscopic image PI, or the DRR image reconstructed after each location or region is input (set). Also, as shown in FIG. 1, the treatment device 10 constituting the treatment system 1 captures fluoroscopic images PI of the patient P in two directions using two imaging devices. Accordingly, the DRR image reconstructed from the CT image also includes two-direction DRR images associated with the two imaging devices. Thus, the region-of-interest acquirer 102 may use the principle of triangulation on the two-direction DRR images and the fluoroscopic image PI to represent the acquired region of interest ROI by coordinates of the three-dimensional space as in the CT image.

Also, a third method of acquiring a region of interest ROI is a method of acquiring a region of interest ROI on the basis of treatment plan information output from the treatment plan acquirer 101. In the case of this method, the region-of-interest acquirer 102 acquires the entire region of the lesion as the region of interest ROI on the basis of, for example, information regarding the position of a lesion and the size of the lesion within the body of the patient P included in the treatment plan information. Also, the region-of-interest acquirer 102 acquires the entire region of the irradiation path of the treatment beam B as the region of interest ROI on the basis of, for example, information regarding the direction (a path) of the treatment beam B to be radiated, the range (the region) to be irradiated with the treatment beam B (an irradiation field), and the position of the lesion and the size of the lesion within the body of the patient P included in the treatment plan information.

In this manner, the region-of-interest acquirer 102 acquires (extracts) the region of interest ROI on the basis of the treatment plan information output from the treatment plan acquirer 101. Also, the final regions of interest ROI may be obtained by combining regions of interest ROI acquired in a plurality of acquisition methods without exclusively performing the above-described three methods of acquiring the region of interest ROI in the region-of-interest acquirer 102. Also, the above-described three methods of acquiring the region of interest ROI in the region-of-interest acquirer 102 are examples. Likewise, any acquisition method may be used to obtain a region of interest ROI as long as a partial region within the body of the patient P can be acquired as the region of interest ROI.

Next, a method of calculating a degree of influence in the degree-of-influence calculator 103 constituting the medical image processing device 100 will be described.

As described above, the degree-of-influence calculator 103 calculates the degree of influence of the treatment beam B on each region of interest ROI up to the range of the treatment beam B on the basis of the treatment plan information output from the treatment plan acquirer 101. At this time, when the region of interest ROI is represented by the coordinates of the three-dimensional space representing the position of each pixel included in the CT image, the degree-of-influence calculator 103 calculates a degree of influence for a position of each pixel included in the region of interest ROI. Also, in this case, the degree-of-influence calculator 103 may calculate the degree of influence while sampling positions of pixels included in the region of interest ROI at predetermined intervals. Also, when the region of interest ROI is represented by the coordinates of the two-dimensional space representing the position of each pixel included in the DRR image or the fluoroscopic image PI, the degree-of-influence calculator 103 calculates the degree of influence for a position of each pixel included in the region of interest ROI. Also, the degree-of-influence calculator 103 may divide the region of interest ROI into regions, each of which has a predetermined size, and calculate the degree of influence for one unit of each of the regions obtained through the division.

Figure 4:
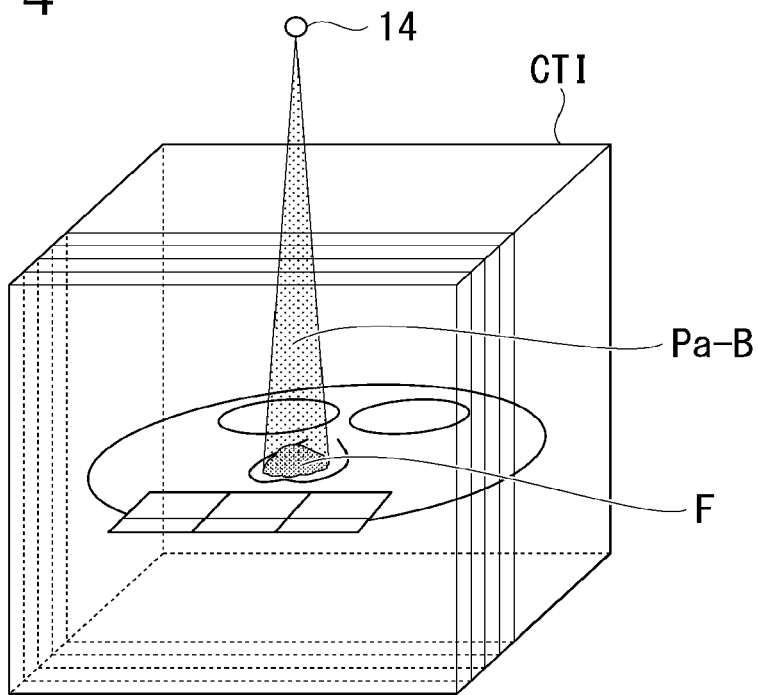
FIG. 4 is a diagram showing an example of a relationship between emission of radiation and an irradiation target of the radiation in a treatment system including the medical image processing device of the first embodiment.

Here, the treatment beam B radiated from the treatment beam irradiation gate 14 in the treatment system 1 will be described. FIG. 4 is a diagram showing an example of a relationship between emission of radiation (the treatment beam B) and an irradiation target (a lesion present within the body of the patient P) of the radiation (the treatment beam B) in the treatment system 1 including the medical image processing device 100 of the first embodiment. In FIG. 4, an example of a region through which the treatment beam B radiated from the treatment beam irradiation gate 14 passes before the treatment beam B reaches an irradiation target lesion is shown. In FIG. 4, an example of a passage region Pa-B through which the treatment beam B passes when the treatment beam irradiation gate 14 and a CT image CTI are virtually arranged in a three-dimensional space and the treatment beam irradiation gate 14 performs scanning irradiation with a single treatment beam B, so that the entire region of the lesion F present within the body of the patient P shown in the CT image CTI is irradiated therewith, is shown.

The passage region Pa-B is a three-dimensional region from the treatment beam irradiation gate 14 to a position where each treatment beam B emitted from the treatment beam irradiation gate 14 and subjected to scanning irradiation reaches the lesion F. Thus, the passage region Pa-B can be regarded as a cone having the apex of the treatment beam irradiation gate 14 as shown in FIG. 4. Also, the passage region Pa-B may be regarded as a cylinder when the path of the treatment beam B is used as an axis. Also, the passage region Pa-B may be regarded as a region obtained by projecting the three-dimensional space shown in FIG. 4 onto a two-dimensional space, i.e., an image such as a DRR image.

The degree-of-influence calculator 103 calculates a degree of influence on the basis of a positional relationship between an irradiation path of the treatment beam B within a region of the passage region Pa-B regarded as described above and a position of each pixel included in the region of interest ROI.

Here, a method of calculating a degree of influence in the degree-of-influence calculator 103 will be described. Also, a plurality of methods can be considered for the method of calculating the degree of influence in the degree-of-influence calculator 103.

A first method of calculating the degree of influence is a method of calculating the degree of influence for each region of interest ROI. In this case, the degree-of-influence calculator 103 calculates the degree of influence determined for each region of interest ROI on the basis of a degree of overlap between the region of interest ROI and the passage region of the treatment beam B such as the passage region Pa-B. More specifically, the degree-of-influence calculator 103 sets a ratio between a volume of a region where the passage region of the treatment beam B overlaps a target region of interest ROI for calculating the degree of influence and a volume of the region of interest ROI as the degree of influence. Alternatively, the degree-of-influence calculator 103 sets the shortest distance between the region of interest ROI and the passage region of the treatment beam B as the degree of influence. The degree-of-influence calculator 103 sets one degree of influence calculated for each region of interest ROI as the degree of influence for the position of each pixel included in the region of interest ROI.

Also, a second method of calculating a degree of influence is a method of calculating a degree of influence for a position of each pixel included in the region of interest ROI. In this case, the degree-of-influence calculator 103 sets the shortest distance between the position of each pixel included in the region of interest ROI and the passage region of the treatment beam B as the degree of influence.

In this manner, the degree-of-influence calculator 103 calculates a degree of influence of the treatment beam B on the region of interest ROI. Also, the above-described two calculation methods of calculating the degree of influence in the degree-of-influence calculator 103 are examples. Likewise, the degree of influence may be calculated using any calculation method in which the degree of influence on the region of interest ROI can be calculated.

Next, a method of generating a display image in the display controller 105 constituting the medical image processing device 100 will be described.

As described above, the display controller 105 generates a display image in which pixels of a location (or a region of the same division) where there is deviation between a position of the patient P shown in a CT image and a position of the patient P shown in a fluoroscopic image PI are highlighted (conspicuous) by superimposing information regarding the degree of influence output from the degree-of-influence calculator 103 on the fluoroscopic image PI output from the image acquirer 104. The display image generated by the display controller 105 is an image in which differentiation by color is made in accordance with a magnitude of the degree of influence on each pixel included in the fluoroscopic image PI output from the image acquirer 104. More specifically, when the degree of influence output from the degree-of-influence calculator 103 is a degree of influence calculated with respect to a position of each pixel included in the region of interest ROI represented by coordinates of a two-dimensional space, i.e., when the position of a pixel for which the degree of influence is obtained is in the two-dimensional space, the display controller 105 colors a pixel associated with the position of each pixel. Also, when the degree of influence output from the degree-of-influence calculator 103 is a degree of influence calculated with respect to a position of each pixel included in the region of interest ROI represented by coordinates of a three-dimensional space, i.e., when the position of a pixel for which the degree of influence is obtained is in the three-dimensional space, the display controller 105 colors a pixel associated with a position where the position of each pixel is projected onto the fluoroscopic image PI. At this time, when there are a plurality of degrees of influence on the same pixel position, the display controller 105 colors each pixel using an average or maximum value of magnitudes of the degrees of influence. Also, the display controller 105 changes the color in which each pixel is colored according to the magnitude of the degree of influence in the pixel. At this time, the display controller 105 changes the color in which each pixel is colored using, for example, a heat map.

Also, as described above, the degree of influence output from the degree-of-influence calculator 103 may be a degree of influence calculated with respect to a region of interest ROI including a region where a predetermined range (width) is further provided around a range (a width) of an irradiation path of the treatment beam B. In this case, the display controller 105 may generate a display image in which the color of pixels included in a region of a range (a width) of an irradiation path of a plurality of treatment beams B for performing scanning irradiation and the color of pixels included in the region of the range (the width) further provided around the irradiation path of the treatment beam B are distinguished by different colors or different color densities.

Also, the display image generated by the display controller 105 is not limited to an image in which the information regarding the degree of influence output from the degree-of-influence calculator 103 is superimposed on the fluoroscopic image PI output from the image acquirer 104. For example, the display controller 105 may generate a display image in which the information regarding the degree of influence output from the degree-of-influence calculator 103 is superimposed on the DRR image reconstructed from the CT image when the degree of influence output from the degree-of-influence calculator 103 is a degree of influence calculated with respect to the position of each pixel included in the region of interest ROI represented by coordinates of the three-dimensional space. In this case, the display controller 105 may reconstruct a DRR image from the CT image output from the treatment plan acquirer 101 as in the region-of-interest acquirer 102 to generate a display image. Also, the region-of-interest acquirer 102 is configured to output the reconstructed DRR image to the display controller 105 and the display controller 105 may generate a display image in which the information regarding the degree of influence output from the degree-of-influence calculator 103 is superimposed on the DRR image output from the region-of-interest acquirer 102. At this time, the display controller 105 may generate a display image by, for example, combining the DRR image with the fluoroscopic image PI and subsequently superimposing the information regarding the degree of influence thereon. Here, a case in which the fluoroscopic image PT and the DRR image are combined by the existing image compositing technology such as alpha blending is conceivable.

Figure 5:
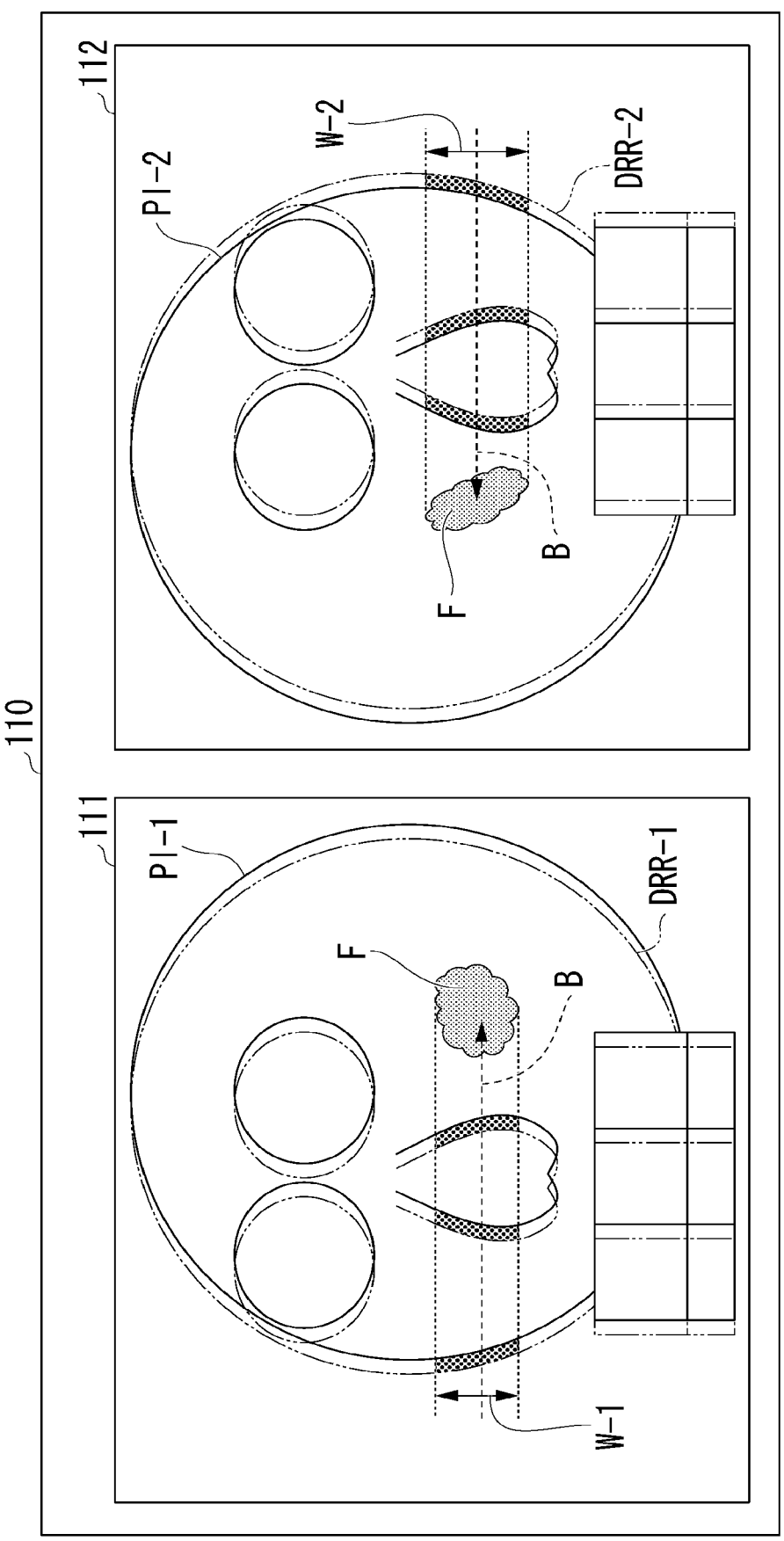
FIG. 5 is a diagram showing an example of a display image generated by a display controller provided in the medical image processing device of the first embodiment.

Here, an example of the display image generated by the display controller 105 will be described. FIG. 5 is a diagram showing an example of a display image generated by the display controller 105 provided in the medical image processing device 100 of the first embodiment. FIG. 5 shows an example of a display image in which information regarding the degree of influence is superimposed after the fluoroscopic image PI and the DRR image are combined.

In FIG. 5, a display image 111 in which information regarding the degree of influence is superimposed on a fluoroscopic image PI-1 captured by the imaging device including the set of the radiation source 12-1 and the radiation detector 13-1 provided in the treatment device 10 is shown on the left side of the display screen 110. A DRR image DRR-1 associated with the fluoroscopic image PI-1 is combined in the display image 111. In the display image 111, pixels of a location where there is deviation between a position of the patient P shown in the DRR image DRR-1 and a position of the patient P shown in the fluoroscopic image PI-1 (a location where a contour portion of a bone of the patient P deviates) are colored and highlighted (conspicuous) in accordance with the associated information regarding a degree of influence within a range (a width) W-1 of an irradiation path along which the lesion F is irradiated with the treatment beam B according to scanning irradiation. Also, the range (the width) W-1 of the irradiation path is a width of the lesion F shown in the DRR image DRR-1 and the fluoroscopic image PI-1. Also, in the display image 111, the treatment beam B with which the center of the lesion F is irradiated is shown as an example of the treatment beam B subjected to scanning irradiation.

Also, in FIG. 5, a display image 112 in which information regarding the degree of influence is superimposed on a fluoroscopic image PI-2 captured by the imaging device including the set of the radiation source 12-2 and the radiation detector 13-2 provided in the treatment device 10 is shown on the right side of the display screen 110. In the display image 112, as in the display image 111, a DRR image DRR-2 associated with the fluoroscopic image PI-2 is combined. In the display image 112, as in the display image 111, pixels of a location where there is deviation between the position of the patient P shown in the DRR image DRR-2 and the position of the patient P shown in the fluoroscopic image PI-2 (a location where a contour portion of a bone of the patient P deviates) are colored and highlighted (conspicuous) in accordance with the associated information regarding the degree of influence within a range (a width) W-2 of the irradiation path along which the lesion F is irradiated with the treatment beam B according to scanning irradiation. Also, the range (the width) W-2 of the irradiation path is a width of the lesion F shown in the DRR image DRR-2 and the fluoroscopic image PI-2. Accordingly, the range (the width) W-2 of the irradiation path is not always the same as the range (the width) W-1 of the irradiation path in the display image 111. Also, in the display image 112, as in the display image 111, the treatment beam B with which the center of the lesion F is irradiated is also shown as an example of the treatment beam B subjected to scanning irradiation.

The radiation treatment provider (the doctor or the like) using the treatment system 1 can easily confirm deviation between a current position of the patient P and a position of the patient P planned in the treatment planning stage from the display image 111 and the display image 112 shown in the display screen 110. The radiation treatment provider (the doctor or the like) can perform the patient positioning work while visually confirming position deviation of the patient P at present from each of the display image 111 and the display image 112. Also, as described above, the medical image processing device 100 sequentially detects deviations from positions of the patient P and sequentially presents information regarding the position deviations of the patient P to the radiation treatment provider (the doctor or the like). Thus, the number of pixels highlighted (conspicuous) in the display image 111 and the display image 112 generated by the display controller 105 gradually decreases as the position deviation of the patient P is eliminated in the patient positioning work, i.e., as the current position of the patient P is aligned with the position of the patient P planned in the treatment planning stage. When the current position of the patient P finally matches the position of the patient P planned in the treatment planning stage, the pixels highlighted (conspicuous) in the display image 111 and the display image 112 disappear. Thereby, the radiation treatment provider (the doctor or the like) who is performing the patient positioning work can easily confirm the end of the patient positioning work.

Also, an example in which pixels of a location where a contour portion of a bone of the patient P deviates are colored and highlighted (conspicuous) in accordance with associated information regarding the degree of influence has been shown in the example of the display image shown in FIG. 5. However, as described above, for example, the region of interest ROI may include the entire region of the lesion F within the body of the patient P, a contour portion of the lesion F, a location where an important organ is present, or a contour portion of an important organ as well as the contour portion of a bone. In this case, in the example of the display image shown in FIG. 5, pixels of a location where the contour portion of the lesion F within the body of the patient P deviates are also colored in accordance with the associated information regarding the degree of influence so that the pixels are highlighted (conspicuous).

Also, as described above, the degree of influence output from the degree-of-influence calculator 103 may be a degree of influence calculated with respect to the region of interest ROI including a region where a predetermined range (width) is further provided around the range (the width) of the irradiation path of the treatment beam B. In this case, as described above, the display controller 105 can cause ranges (widths) to be distinguished by setting a color for coloring pixels within a range (a width) of the irradiation path along which the lesion F is irradiated with the treatment beam B according to scanning irradiation and a color for coloring pixels within a range (a width) further provided around the irradiation path of the treatment beam B to different colors.

Figure 6:
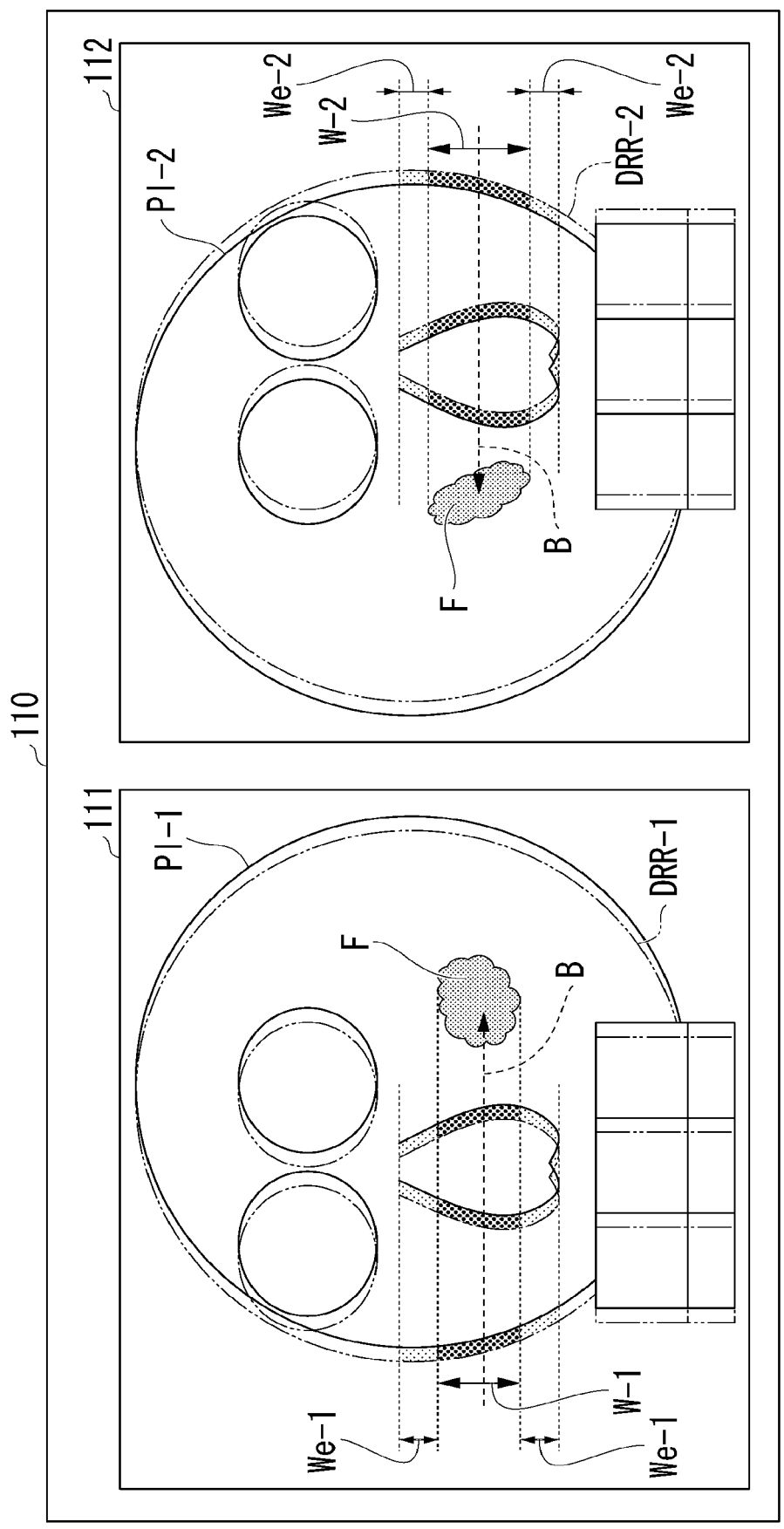
FIG. 6 is a diagram showing another example of a display image generated by the display controller provided in the medical image processing device of the first embodiment.

Here, another example of a display image generated by the display controller 105 will be described. FIG. 6 is a diagram showing the other example of the display image generated by the display controller 105 provided in the medical image processing device 100 of the first embodiment. In FIG. 6, as in the example of the display image shown in FIG. 5, an example of a display image in which information regarding a degree of influence is superimposed after a fluoroscopic image PI and a DRR image are combined is shown.

In FIG. 6, as in the example of the display image 111 shown in FIG. 5, a display image 111 in which a fluoroscopic image PI-1 and an associated DRR image DRR-1 are combined and information regarding a degree of influence is superimposed thereon is shown on the left side of the display screen 110. In the display image 111 shown in FIG. 6, as in the example of the display image 111 shown in FIG. 5, pixels of a location where there is deviation between the position of the patient P shown in the DRR image DRR-1 and the position of the patient P shown in the fluoroscopic image PI-1 (a location where a contour portion of a bone of the patient P deviates) are also colored and highlighted (conspicuous) in accordance with the associated information regarding a degree of influence within a range (a width) W-1 of the irradiation path of the treatment beam B. In the display image 111 shown in FIG. 6, as in the example of the display image 111 shown in FIG. 5, the treatment beam B with which the center of the lesion F is irradiated is also shown as an example of the treatment beam B subjected to scanning irradiation. Further, in the display image 111 shown in FIG. 6, pixels of a location where there is deviation between the position of the patient P shown in the DRR image DRR-1 and the position of the patient P shown in the fluoroscopic image PI-1 (a location where a contour portion of a bone of the patient P deviates) within a range (a width) We-1 provided around the range (the width) W-1 of the irradiation path of the treatment beam B are colored in a color different from that of pixels within the range (the width) W-1 of the irradiation path. Thereby, in the display image 111, pixels within a range (a width) including the range (the width) We-1 are highlighted (conspicuous) and the range (the width) W-1 of the irradiation path of the treatment beam B and the range (the width) We-1 are distinguished. Also, the region within the range (the width) We-1 has a lower degree of importance for irradiating the lesion F with the treatment beam B in the radiation treatment than the region within the range (the width) W-1 of the irradiation path. Thus, for example, a case in which a color for coloring the pixels within the range (the width) We-1 is lighter than a color for coloring the pixels within the range (the width) W-1 of the irradiation path is conceivable.

Also, in FIG. 6, as in the example of the display image 112 shown in FIG. 5, a display image 112 in which a fluoroscopic image PI-2 and an associated DRR image DRR-2 are combined and information regarding a degree of influence is superimposed thereon is shown on the right side of the display screen 110. In the display image 112 shown in FIG. 6, as in the example of the display image 112 shown in FIG. 5, pixels of a location where there is deviation between the position of the patient P shown in the DRR image DRR-2 and the position of the patient P shown in the fluoroscopic image PI-2 (a location where a contour portion of a bone of the patient P deviates) are also colored and highlighted (conspicuous) in accordance with the associated information regarding a degree of influence within a range (a width) W-2 of the irradiation path of the treatment beam B. In the display image 112 shown in FIG. 6, as in the example of the display image 112 shown in FIG. 5, the treatment beam B with which the center of the lesion F is irradiated is also shown as an example of the treatment beam B subjected to scanning irradiation. Further, in the display image 112 shown in FIG. 6, as in the example of the display image 111 shown in FIG. 6, pixels of a location where there is deviation between the position of the patient P shown in the DRR image DRR-2 and the position of the patient P shown in the fluoroscopic image PI-2 (a location where a contour portion of a bone of the patient P deviates) within a range (a width) We-2 provided around the range (the width) W-2 of the irradiation path of the treatment beam B are also colored in a color different from that of pixels within the range (the width) W-2 of the irradiation path. Thereby, in the display image 112 shown in FIG. 6, as in the example of the display image 111 shown in FIG. 6, pixels within a range (a width) including the range (the width) We-2 are highlighted (conspicuous) and the range (the width) W-2 of the irradiation path of the treatment beam B and the range (the width) We-2 are distinguished. Also, the region within the range (the width) We-2 has a lower degree of importance for irradiating the lesion F with the treatment beam B in the radiation treatment than the region within the range (the width) W-2 of the irradiation path as in the region within the range (the width) We-1 in the display image 111 shown in FIG. 6. Thus, a case in which a color for coloring the pixels within the range (the width) We-2 is also lighter than a color of coloring the pixels within the range (the width) W-2 of the irradiation path as in the region within the range (the width) We-1 in the display image 111 shown in FIG. 6 is conceivable.

The radiation treatment provider (the doctor or the like) using the treatment system 1 can easily confirm deviation between a current position of the patient P and a position of the patient P planned in the treatment planning stage from the display image 111 and the display image 112 shown in the display screen 110 shown in FIG. 6 and can perform patient positioning work while visually confirming position deviation of the patient P at present. Also, even if the patient positioning work is performed using the display image 111 and the display image 112 shown in the display screen 110 shown in FIG. 6, the number of highlighted (conspicuous) pixels gradually decreases as the position deviation of the patient P is eliminated as in a case in which the patient positioning work is performed using the display image 111 and the display image 112 shown in the display screen 110 shown in FIG. 5. Even if the patient positioning work is performed using the display image 111 and the display image 112 shown in the display screen 110 shown in FIG. 6, the radiation treatment provider (the doctor or the like) who performs the patient positioning work can easily confirm the end of the patient positioning work. Moreover, when the patient positioning work is performed using the display image 111 and the display image 112 shown in the display screen 110 shown in FIG. 6, the current position of the patient P can be more strictly aligned with the position of the patient P planned in the treatment planning stage because position alignment of the patient P is performed with respect to a wider range.

Also, in the example of the display image shown in FIG. 6, as in the example of the display image shown in FIG. 5, an example in which pixels of a location where a contour portion of a bone of the patient P deviates are colored and highlighted (conspicuous) in accordance with the associated information regarding the degree of influence has also been shown. However, as described above, for example, the region of interest ROI may include the entire region of the lesion F within the body of the patient P, a contour portion of the lesion F, a location where an important organ is present, or a contour portion of an important organ as well as the contour portion of a bone. In this case, in the example of the display image shown in FIG. 6, as in the example of the display image shown in FIG. 5, pixels of a location where the contour portion of the lesion F within the body of the patient P deviates are also colored in accordance with the associated information regarding the degree of influence so that the pixels are highlighted (conspicuous).

The display controller 105 generates this display image and presents the generated display image to the radiation treatment provider (the doctor or the like) using the treatment system 1. Also, the display images shown in FIGS. 5 and 6 are examples and the display controller 105 may generate a display image using any display method in which information representing deviation between the current position of the patient P and the position of the patient P planned in the treatment planning stage can be presented. For example, when pixels of a location where a position within the range (the width) of the irradiation path of the treatment beam B deviates are colored, different colors may be used on the front side and the back side of the patient P. Thereby, the radiation treatment provider (the doctor or the like) who performs the patient positioning work can easily three-dimensionally confirm a position of the patient P that has deviated. In this case, the radiation treatment provider (the doctor or the like) can further assign priority to a location to efficiently perform the patient positioning work even if there are locations where a position deviates within the same range (width) of the irradiation path of the treatment beam as in a case in which the back side of the patient P is aligned after the front side of the patient P is first aligned or the like when the patient positioning work is performed. Also, a method of causing a location where a position deviates within a range (a width) of the irradiation path of the treatment beam B to be highlighted (conspicuous) is not limited to a method of coloring pixels. A location where a position deviates may be represented by a pattern (a checkerboard pattern or the like).

As described above, in the medical image processing device 100 of the first embodiment, the treatment plan acquirer 101 acquires treatment plan information made in the treatment planning stage. In the medical image processing device 100 of the first embodiment, the region-of-interest acquirer 102 acquires (extracts) a location where position deviation is large within a region around the irradiation path of the treatment beam B with which the lesion within the body of the patient P is irradiated as a region of interest ROI on the basis of the treatment plan information. Thereby, in the medical image processing device 100 of the first embodiment, the radiation detector 13 calculates a degree of influence when a location (the region of interest ROI) where the position deviation is large is irradiated with the treatment beam B up to a range within an irradiation path along which the lesion within the body of the patient P is irradiated with the treatment beam B on the basis of the treatment plan information. Subsequently, in the medical image processing device 100 of the first embodiment, the display controller 105 generates a display image in which a location where position deviation within the irradiation path of the treatment beam B considered to be important in the patient positioning work is large is highlighted (conspicuous) in accordance with information regarding a degree of influence in a current fluoroscopic image PI of the patient P acquired by the image acquirer 104. Thereby, in the medical image processing device 100 of the first embodiment, the radiation treatment provider (the doctor or the like) using the treatment system 1 can perform the patient positioning work while visually and easily confirming deviation between a current position of the patient P and a position of the patient P planned in the treatment planning stage from the display image displayed on the display device (not shown). Thereby, the medical image processing device 100 of the first embodiment can appropriately determine a result of the patient positioning work.

As described above, the medical image processing device 100 includes the region-of-interest acquirer 102 configured to acquire a partial region within a body of the patient P as a region of interest ROI; the treatment plan acquirer 101 configured to acquire treatment plan information determined in a planning stage of radiation treatment to be performed on the patient P; the degree-of-influence calculator 103 configured to calculate a degree of influence representing an influence on the region of interest ROI up to a range until radiation (a treatment beam B) with which the patient P is irradiated reaches a target portion (a lesion) to be treated within the body of the patient P; and the display controller 105 configured to generate a display image in which information regarding the degree of influence is superimposed on a current fluoroscopic image PI of the patient P and cause a display to display the display image.

Also, as described above, the degree-of-influence calculator 103 may calculate the degree of influence on the basis of a degree of overlap between a passage path of the treatment beam B that is radiated and the region of interest ROI.

Also, as described above, the degree-of-influence calculator 103 may calculate the degree of influence on the basis of a ratio between a volume in which the passage path of the treatment beam B that is radiated overlaps the region of interest ROI and the volume of the region of interest ROI.

Also, as described above, the degree-of-influence calculator 103 may calculate the degree of influence on the basis of the shortest distance between the passage path of the treatment beam B that is radiated and the region of interest ROI.

Also, as described above, the region-of-interest acquirer 102 may acquire a location where deviation between a region of the patient P shown in a plan image (for example, a CT image) captured in the planning stage and a region of the patient P shown in the fluoroscopic image PI is greater than a predetermined threshold value as the region of interest ROI.

Also, as described above, the region-of-interest acquirer 102 may acquire a location within a range of an irradiation path of the treatment beam B among locations where region deviation is greater than the threshold value as the region of interest ROI.

Also, as described above, the region-of-interest acquirer 102 may acquire a location including a predetermined range provided around the range of the irradiation path of the treatment beam B as the region of interest ROI.

Also, as described above, the display controller 105 may generate the display image in which pixels associated with the region of interest ROI within the range of the irradiation path of the treatment beam B among pixels of the fluoroscopic image PI are highlighted in accordance with information regarding the degree of influence.

Also, as described above, the display controller 105 may generate the display image in which a color of the pixels to be highlighted (conspicuous) is changed.

Also, as described above, the display controller 105 may generate the display image in which the pixels to be highlighted (conspicuous) are highlighted (conspicuous) in accordance with information regarding the degree of influence after a reconstructed image (for example, a DDR image) having the same range as the fluoroscopic image PI virtually reconstructed from a plan image (for example, a CT image) captured in the planning stage is combined with the fluoroscopic image PI.

Also, as described above, the display controller 105 may generate the display image in which pixels within a predetermined range provided around the range of the irradiation path of the treatment beam B among pixels of the fluoroscopic image PI are highlighted (conspicuous) in a method different from that of the pixels to be highlighted (conspicuous).

Further, as described above, the treatment system 1 may include the medical image processing device 100; the treatment device 10 including an irradiator (the treatment beam irradiation gate 14) configured to irradiate a target portion (a lesion) to be treated with the radiation (the treatment beam B) and an imaging device (the set of the radiation source 12 and the radiation detector 13) configured to capture the fluoroscopic image PI; and a display device (not shown) configured to display the display image.

Also, the medical image processing device 100 includes a processor such as a CPU or a GPU and a storage device such as a ROM, a RAM, an HDD, or a flash memory. The storage device may be a device storing a program for causing the processor to function as: the region-of-interest acquirer 102 configured to acquire a partial region within a body of the patient P as a region of interest ROI; the treatment plan acquirer 101 configured to acquire treatment plan information determined in a planning stage of radiation treatment to be performed on the patient P; the degree-of-influence calculator 103 configured to calculate a degree of influence representing an influence on the region of interest ROI up to a range until a treatment beam B with which the patient P is irradiated reaches a target portion (a lesion) to be treated within the body of the patient P; and the display controller 105 configured to generate a display image in which information regarding the degree of influence is superimposed on a current fluoroscopic image PI of the patient P and cause a display to display the display image.

Second Embodiment

Hereinafter, a second embodiment will be described. The configuration of a treatment system including a medical image processing device of the second embodiment is a configuration in which the medical image processing device 100 in the configuration of the treatment system 1 including the medical image processing device 100 of the first embodiment shown in FIG. 1 is replaced with a medical image processing device of the second embodiment (hereinafter referred to as a "medical image processing device 200"). In the following description, the treatment system including the medical image processing device 200 is referred to as a "treatment system 2."

Also, in the following description, the components of the treatment system 2 including the medical image processing device 200 similar to those of the treatment system 1 including the medical image processing device 100 of the first embodiment are denoted by the same reference signs and a detailed description of similar components will be omitted. In the following description, only a configuration, an operation, and a process of the medical image processing device 200, which is a component different from the medical image processing device 100 of the first embodiment, will be described.

In the treatment system 2, a treatment beam irradiation gate 14 provided in the treatment device 10 is configured to move to rotate around a patient P and irradiate the patient P with treatment beams in various directions (at various angles).

The medical image processing device 200 irradiates a lesion within the body of the patient P to be treated in the radiation treatment with a treatment beam B on the basis of a fluoroscopic images PI output from a radiation detector 13-1 and a radiation detector 13-2 as in the medical image processing device 100 of the first embodiment. Thereby, the medical image processing device 200 tracks an organ, which moves due to the motion of respiration or heartbeat of the patient P, such as the lung or the liver and causes the treatment beam irradiation gate 14 to irradiate the lesion within the body of the patient P with the treatment beam B at an appropriate timing as in the medical image processing device 100 of the first embodiment. Also, tracking of the lesion in the medical image processing device 200 is performed on the basis of a CT image or a fluoroscopic image PI of the patient P captured before the radiation treatment is performed in a stage such as the treatment planning stage and a current fluoroscopic image PI of the patient P as in tracking of a lesion in the medical image processing device 100 of the first embodiment.

Also, the medical image processing device 200 presents information regarding the position of the patient P to be confirmed in the patient positioning work performed by a radiation treatment provider (a doctor or the like) using the treatment system 2 before the treatment is started as in the medical image processing device 100 of the first embodiment. At this time, the medical image processing device 200 also sequentially detects deviations between current positions of the patient P laid on a treatment table 11 and positions of the patient P planned at the time of the treatment planning on the basis of the CT image or the fluoroscopic image PI of the patient P captured in the treatment planning stage and the current fluoroscopic image PI of the patient P as in the medical image processing device 100 of the first embodiment. The medical image processing device 200 also sequentially presents information representing the detected position deviations of the patient P to the radiation treatment provider (the doctor or the like) using the treatment system 2 as in the medical image processing device 100 of the first embodiment. Also, in the treatment system 2, as described above, the treatment beam irradiation gate 14 is configured to move to rotate around the patient P. Thus, in the medical image processing device 200, information representing a direction (an angle) in (at) which the treatment beam irradiation gate 14 radiates the treatment beam B is also presented to the radiation treatment provider (the doctor or the like) using the treatment system 2.

Figure 7:
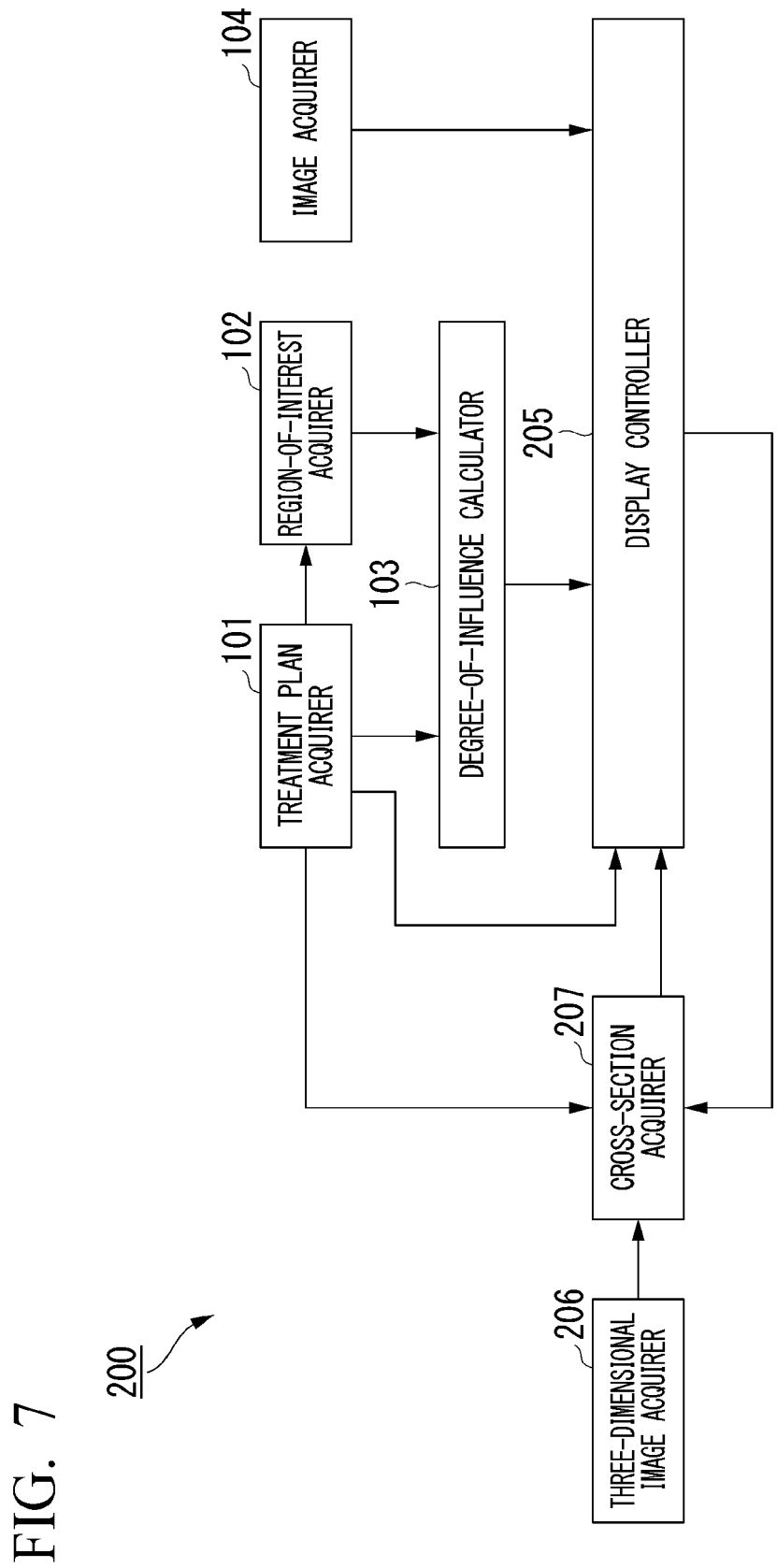
FIG. 7 is a block diagram showing a schematic configuration of a medical image processing device of a second embodiment.

Hereinafter, a configuration of the medical image processing device 200 constituting the treatment system 2 will be described. FIG. 7 is a block diagram showing a schematic configuration of the medical image processing device 200 of the second embodiment. Also, in FIG. 7, only a configuration related to a function of presenting information representing position deviation of the patient P confirmed by the radiation treatment provider (the doctor or the like) using the treatment system 2 when patient positioning work is performed is shown. The medical image processing device 200 shown in FIG. 7 includes a treatment plan acquirer 101, a region-of-interest acquirer 102, and a degree-of-influence calculator 103, an image acquirer 104, a three-dimensional image acquirer 206, a cross-section acquirer 207, and a display controller 205 as components for implementing a function of presenting information representing the position deviation of the patient P.

The medical image processing device 200 has a configuration in which the three-dimensional image acquirer 206 and the cross-section acquirer 207 are added to the medical image processing device 100 of the first embodiment. In association with this, in the medical image processing device 200, the display controller 105 provided in the medical image processing device 100 of the first embodiment is replaced with the display controller 205. The other components provided in the medical image processing device 200 are the same as those provided in the medical image processing device 100 of the first embodiment. Accordingly, in the following description, the components of the medical image processing device 200 similar to those provided in the medical image processing device 100 of the first embodiment are denoted by the same reference signs and a detailed description of similar components will be omitted. In the following description, only components different from those of the medical image processing device 100 of the first embodiment will be described.

The treatment plan acquirer 101 acquires treatment plan information and outputs the acquired treatment plan information to each of the region-of-interest acquirer 102, the degree-of-influence calculator 103, and the cross-section acquirer 207. Also, the treatment plan information acquired by the treatment plan acquirer 101 in the medical image processing device 200 also includes information regarding the position where the treatment beam irradiation gate 14 moves while rotating around the patient P, i.e., a direction (an angle) in (at) which the treatment beam irradiation gate 14 radiates the treatment beam B in the treatment.

The three-dimensional image acquirer 206 acquires an image of three dimensions (hereinafter referred to as "three-dimensional image"). Here, the three-dimensional image acquired by the three-dimensional image acquirer 206 is either or both of a three-dimensional image such as a CT image used in the treatment plan and a three-dimensional image such as a CT image captured in the previous radiation treatment. Also, the three-dimensional image may be any image from which a structure within the body of the patient P can be three-dimensionally ascertained. For example, the three-dimensional image may be a three-dimensional image (a magnetic resonance imaging (MRI) image) captured by an MRI imaging device for performing photography of MRI. The three-dimensional image acquirer 206 outputs the acquired three-dimensional image to the cross-section acquirer 207.

The cross-section acquirer 207 acquires the treatment plan information output from the treatment plan acquirer 101, the three-dimensional image output from the three-dimensional image acquirer 206, and the control signal output from the display controller 205. The cross-section acquirer 207 acquires (generates) cross-sectional images of three-dimensional images obtained by segmenting one or more planes within a three-dimensional space on the basis of the treatment plan information or the control signal that has been acquired. More specifically, the cross-section acquirer 207 acquires (generates) a cross-sectional image obtained by segmenting a plane of an irradiation direction of the treatment beam B from the three-dimensional space on the basis of a position of a tumor (a lesion) within the body of the patient P included in the treatment plan information and information regarding the direction (the angle) in (at) which the treatment beam B is radiated in the treatment. Also, the cross-section acquirer 207 acquires (generates) a cross-sectional image obtained by segmenting a plane of the irradiation direction of the treatment beam B from the three-dimensional space on the basis of a position of the treatment beam irradiation gate 14 included in the treatment plan information, i.e., an irradiation position of the treatment beam B, and a specific position within the body of the patient P represented by the control signal. The cross-section acquirer 207 outputs the acquired (generated) cross-sectional image of the three-dimensional image to the display controller 205.

The display controller 205 generates a display image in which information regarding the degree of influence output from the degree-of-influence calculator 103 is superimposed on a fluoroscopic image PI output from the image acquirer 104 as in the display controller 105 provided in the medical image processing device 100 of the first embodiment. Also, the display controller 205 generates the cross-sectional image of the three-dimensional image output from the cross-section acquirer 207 as the display image. The display controller 205 outputs each of generated display images to a display device (not shown), thereby causing the display device (not shown) to display each of the display images. Also, the display controller 205 outputs a control signal representing an indicated position to the cross-section acquirer 207, for example, when a specific position within the cross-sectional image is indicated by the radiation treatment provider (the doctor or the like). Thereby, the cross-section acquirer 207 generates a cross-sectional image of a new three-dimensional image according to the control signal and the display controller 205 generates the cross-sectional image of the new three-dimensional image output from the cross-section acquirer 207 as a display image and outputs the display image to the display device (not shown), thereby causing the display device (not shown) to display the display image.

According to this configuration, the medical image processing device 200 causes the display device (not shown) to display a display image in which pixels of a location where position deviation of the patient P is present are highlighted (conspicuous) in accordance with information regarding the associated degree of influence in consideration of the irradiation path of the treatment beam B important in the patient positioning work to be performed before the treatment is started and sequentially presents display images to the radiation treatment provider (the doctor or the like) using the treatment system 2 as in the medical image processing device 100 of the first embodiment. Also, the medical image processing device 200 also presents information (a cross-sectional image) representing a direction in which the treatment beam irradiation gate 14 radiates the treatment beam B to the radiation treatment provider (the doctor or the like) using the treatment system 2. Thereby, the radiation treatment provider (the doctor or the like) using the treatment system 2 can perform the patient positioning work while visually comparing (confirming) information regarding the position deviations of the patient P sequentially presented from the medical image processing device 200 and information representing a direction (a cross-sectional image) in which the treatment beam irradiation gate 14 radiates the treatment beam B.

Figure 8:
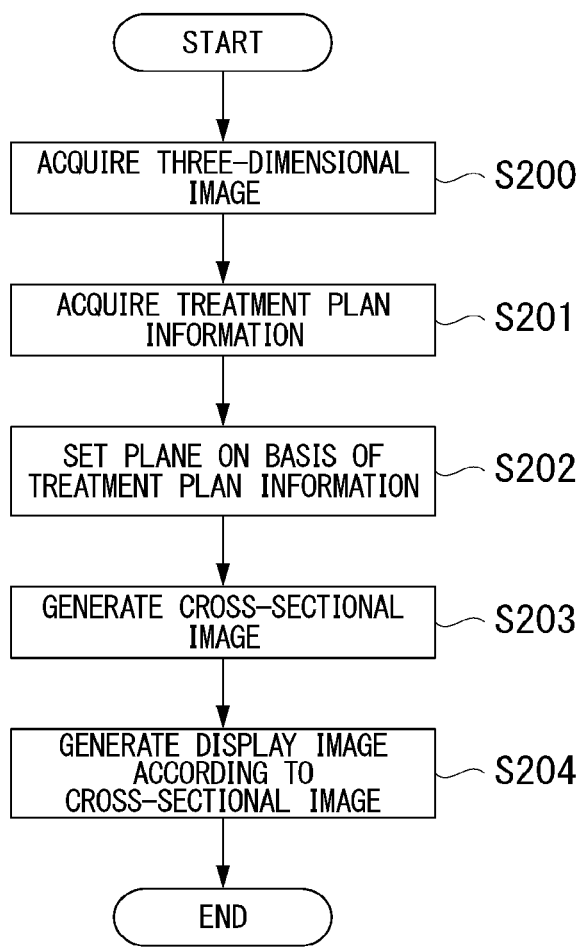
FIG. 8 is a flowchart showing a flow of an operation of the medical image processing device of the second embodiment.
Figure 9:
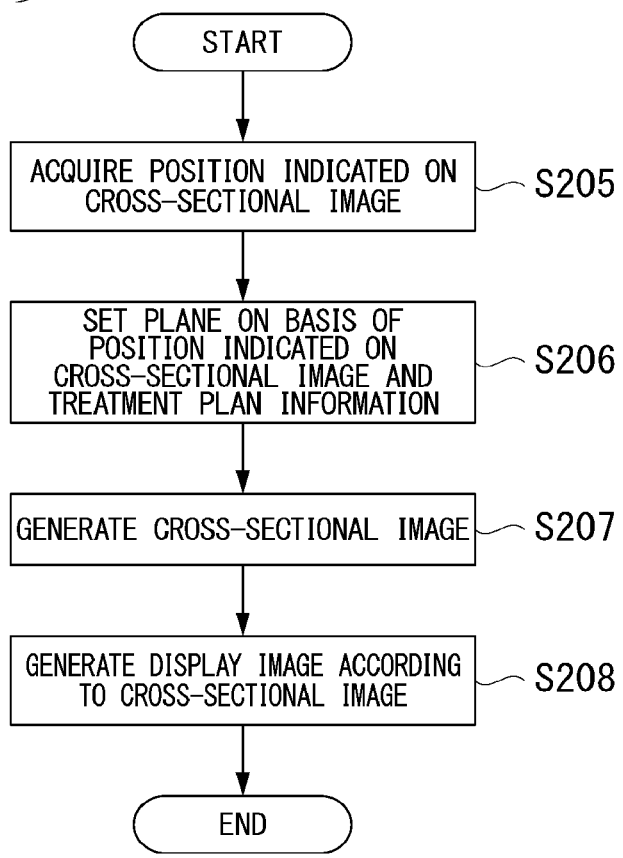
FIG. 9 is a flowchart showing a flow of another operation of the medical image processing device of the second embodiment.

Here, an operation of the medical image processing device 200 constituting the treatment system 2 will be schematically described. Also, in the following description, an operation in which the medical image processing device 200 presents information (a cross-sectional image) representing a direction in which the treatment beam irradiation gate 14 radiates the treatment beam B to the radiation treatment provider (the doctor or the like) using the treatment system 2 for performing the patient positioning work will be schematically described. FIGS. 8 and 9 are examples of a flowchart showing a flow of the operation of the medical image processing device 200 of the second embodiment. The example of the flow of the operation when the treatment system 2 is activated, i.e., when the medical image processing device 200 is activated, is shown in FIG. 8. Also, the example of the flow of the operation of the medical image processing device 200 when the radiation treatment provider (the doctor or the like) indicates a specific position on the displayed cross-sectional image is shown in FIG. 9.

First, the operation when the medical image processing device 200 is activated will be described with reference to FIG. 8. When the medical image processing device 200 is activated, the three-dimensional image acquirer 206 first acquires a three-dimensional image (step S200). Subsequently, the treatment plan acquirer 101 acquires treatment plan information (step S201). Subsequently, the cross-section acquirer 207 sets a plane within a three-dimensional space on the basis of the treatment plan information output from the treatment plan acquirer 101 (step S202). Subsequently, the cross-section acquirer 207 acquires (generates) a cross-sectional image of a three-dimensional image obtained by segmenting the set plane within the three-dimensional space (step S203). Subsequently, the display controller 205 generates a display image of the cross-sectional image of the three-dimensional image output from the cross-section acquirer 207 (step S204).

Next, the operation of the medical image processing device 200 when the radiation treatment provider (the doctor or the like) indicates a specific position on the displayed cross-sectional image will be described with reference to FIG. 9. If the radiation treatment provider (the doctor or the like) indicates (inputs) the specific position within the displayed cross-sectional image when the display image of the cross-sectional image of the three-dimensional image is displayed on the display device (not shown), the display controller 205 acquires the indicated (input) specific position (step S205). Also, here, it is assumed that the specific position on the cross-sectional image is indicated (input) by the radiation treatment provider (the doctor or the like). The display controller 205 outputs a control signal representing the indicated (input) specific position to the cross-section acquirer 207. Subsequently, the cross-section acquirer 207 sets the plane within the three-dimensional space of the specific position indicated by the radiation treatment provider (the doctor or the like) on the basis of the control signal output from the display controller 205 and the treatment plan information output from the treatment plan acquirer 101 (step S206). Subsequently, the cross-section acquirer 207 acquires (generates) a cross-sectional image of a three-dimensional image obtained by segmenting the set plane within the three-dimensional space (a plane of the indicated specific position) (step S207). Also, the processing of step S207 in the cross-section acquirer 207 is similar to the processing of step S203 when the medical image processing device 200 shown in FIG. 8 is activated, except that the target plane for acquiring (generating) the cross-sectional image is different. Subsequently, the display controller 205 generates a display image of the cross-sectional image of the three-dimensional image (a cross-sectional image of the plane of the indicated specific position) output from the cross-section acquirer 207 (step S208). Also, the processing of step S208 in the display controller 205 is similar to the processing of step S204 when the medical image processing device 200 shown in FIG. 8 is activated, except that the cross-sectional image for generating the display image is different.

Next, the operation of the medical image processing device 200 constituting the treatment system 2 will be described in detail. Here, a method of setting a plane and segmenting a cross-sectional image in the cross-section acquirer 207 constituting the medical image processing device 200 will be described. The method of segmenting the plane set on the basis of only the treatment plan information from the three-dimensional space and the method of segmenting the plane set on the basis of the treatment plan information and the control signal from the three-dimensional space as described above are used when the cross-section acquirer 207 segments the cross-sectional image.

Figure 10:
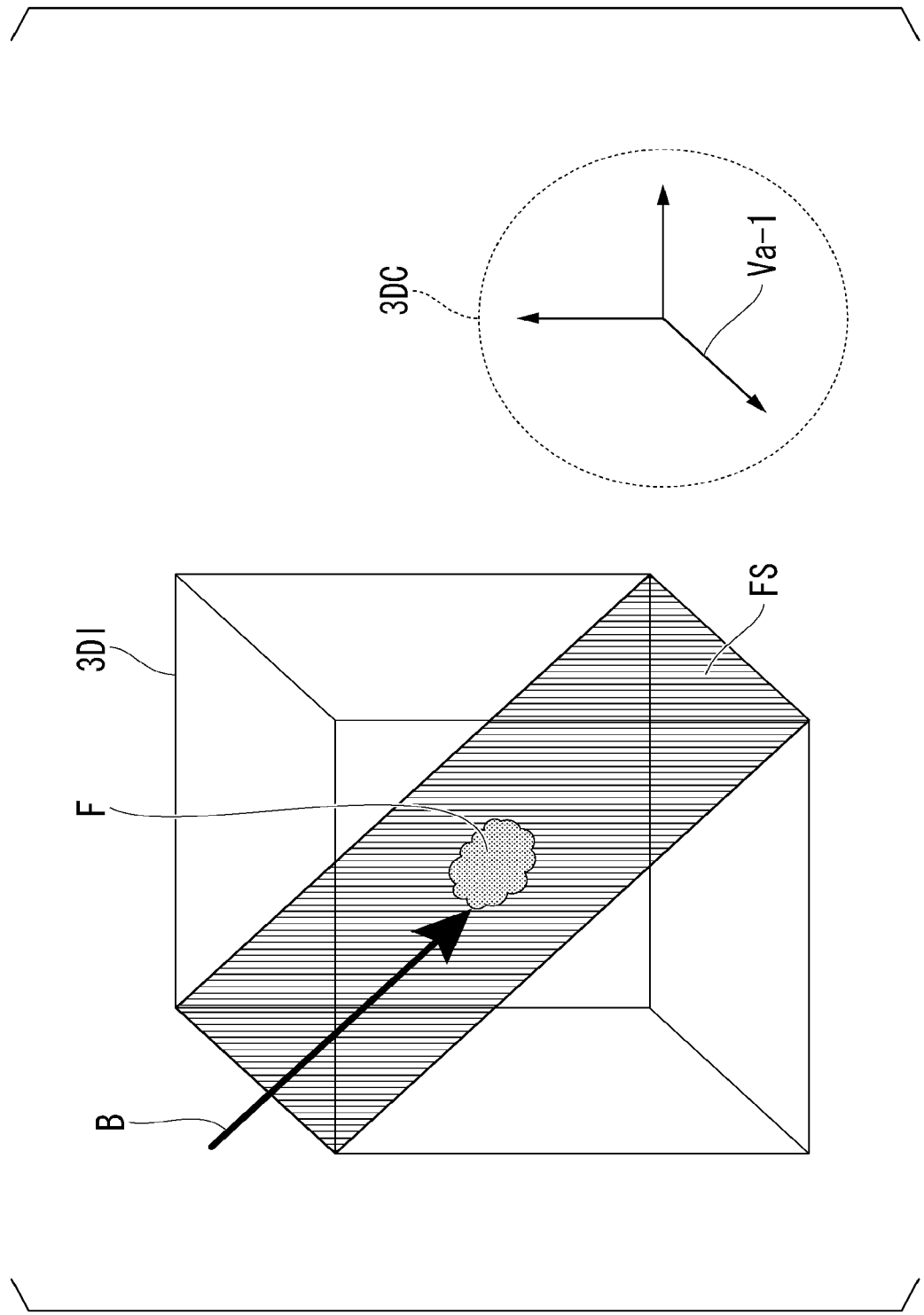
FIG. 10 is a diagram showing an example of a relationship between emission of radiation and an irradiation target of the radiation in a treatment system including the medical image processing device of the second embodiment.

First, the method in which the cross-section acquirer 207 sets the plane on the basis of only treatment plan information and segments the set plane from the three-dimensional space will be described. FIG. 10 is a diagram showing an example of a relationship between emission of radiation (a treatment beam B) and an irradiation target (a lesion present within the body of the patient P) of the radiation (the treatment beam B) in the treatment system 2 including the medical image processing device 200 of the second embodiment. An example of a relationship between a direction (an angle) of the treatment beam B radiated by the treatment beam irradiation gate 14 and a plane set and segmented by the cross-section acquirer 207 is shown in FIG. 10.

The plane set by the cross-section acquirer 207 to segment the cross-sectional image can be set by determining two vectors among non-parallel or vertical three-dimensional vectors within the three-dimensional space. One of the two three-dimensional vectors is a vector representing the irradiation direction of the treatment beam B. Here, a vector parallel to a path through which the radiated treatment beam B passes is referred to as a "primary vector." Also, the primary vector may be used as a direction vector of a straight line for connecting any position within the body of the patient P (for example, the position of the lesion F within the body of the patient P) from the position of the treatment beam irradiation gate 14 that emits the treatment beam B. Also, the other vector of the two vectors of the three-dimensional vectors may determine a vector representing any direction. For example, one of axial direction vectors in the three-dimensional coordinates for which the position of the patient P or the position of the treatment beam irradiation gate 14 can be comprehensively handled may be adopted. Here, for example, the three-dimensional coordinates for which the position of the patient P or the position of the treatment beam irradiation gate 14 can be comprehensively handled are coordinates of a three-dimensional coordinate system defined on the basis of a reference position preset in a treatment room in which the treatment system 2 is installed. Accordingly, the other vector of the two vectors of the three-dimensional vectors is any axial vector in the three-dimensional coordinate system defined in the treatment room where the treatment system 2 is installed. An example of this case is shown in FIG. 10. In FIG. 10, the three-dimensional image 3DI of the patient P is arranged within a certain three-dimensional coordinate system 3DC and the direction of the treatment beam B with which the lesion F within the body of the patient P is irradiated is shown. The cross-section acquirer 207 sets a plane FS using a primary vector represented by the irradiation direction of the treatment beam B and a three-dimensional vector defining a certain axis Va-1 of the three-dimensional coordinate system 3DC. An example of the plane FS set by the cross-section acquirer 207 using the irradiation direction of the treatment beam B and the three-dimensional vector defining the axis Va-1 is shown in FIG. 10.

Also, when there are a plurality of primary vectors representing the irradiation direction of the treatment beam B as in scanning irradiation, the cross-section acquirer 207 sets primary vectors, i.e., a plurality of planes FS associated with treatment beams B in irradiation directions.

The cross-section acquirer 207 acquires (generates) a cross-sectional image by segmenting the plane FS set as shown in FIG. 10 from the three-dimensional image 3DI. This cross-sectional image is an image in which a value of voxel data of the three-dimensional image 3DI located on the set plane FS becomes a value of luminance (a luminance value) in each pixel. Also, the cross-section acquirer 207 may assign information included in the treatment plan information to the cross-sectional image. For example, information regarding the region of a path through which the treatment beam B passes, the position of a lesion F, the region of a contour portion of the lesion F, the position of an important organ, the region of a contour portion of the important organ, or the like is considered for the treatment plan information assigned to the cross-sectional image by the cross-section acquirer 207. Also, for example, a method of superimposing an image representing each piece of information (a region) on the cross-sectional image and the like can be considered for a method in which the cross-section acquirer 207 assigns information.

Next, a method in which the cross-section acquirer 207 sets a plane on the basis of the treatment plan information and the control signal and segments the set plane from the three-dimensional space will be described. That is, a method in which the cross-section acquirer 207 segments a cross-sectional image of a specific position indicated (input) by the radiation treatment provider (the doctor or the like) will be described.

The radiation treatment provider (the doctor or the like) indicates (inputs) a specific position within the displayed cross-sectional image using, for example, an external input means such as a user interface for inputting information, when a cross-sectional image of a three-dimensional image is displayed on the display device (not shown). The display controller 205 outputs a control signal representing the indicated (input) specific position to the cross-section acquirer 207. The cross-section acquirer 207 sets a direction vector of a straight line for connecting a specific position (a position of one point) represented by the control signal output from the display controller 205 and a position of the treatment beam irradiation gate 14 that emits the treatment beam B included in the treatment plan information as the primary vector. The cross-section acquirer 207 resets the plane FS as in the method of setting the plane on the basis of only the above-described treatment plan information and segmenting the cross-sectional image from the three-dimensional space. That is, the cross-section acquirer 207 resets the plane FS as shown in FIG. 10 using the position of the lesion F shown in FIG. 10 as a specific position indicated (input) by the radiation treatment provider (the doctor or the like).

The cross-section acquirer 207 acquires (generates) a cross-sectional image by segmenting the reset plane FS from the three-dimensional image 3DI as in the above-described method of setting the plane on the basis of only the treatment plan information and segmenting the cross-sectional image from the three-dimensional space.

Also, when the radiation treatment provider (the doctor or the like) indicates (inputs) a plurality of specific positions within the displayed cross-sectional image, the display controller 205 outputs a control signal representing each specific position that has been indicated (input) to the cross-section acquirer 207. In this case, the cross-section acquirer 207 resets the plurality of planes FS from the primary vector associated with each of the plurality of specific positions represented by the control signal output from the display controller 205 and acquires (generates) a plurality of cross-sectional images by segmenting the reset planes FS from the three-dimensional image 3DI.

Thereby, the cross-section acquirer 207 sets the plane FS on the basis of only the treatment plan information or the treatment plan information and the control signal (the specific position indicated (input) by the radiation treatment provider (the doctor or the like)) and acquires (generates) a cross-sectional image obtained by segmenting the set plane FS from the three-dimensional image 3DI. Also, the above-described method of setting the plane FS and segmenting the cross-sectional image in the cross-section acquirer 207 is an example and a cross-sectional image may be acquired (generated) using any method in which a cross-sectional image obtained by segmenting a part of the plane region within the body of the patient P can be acquired (generated).

The display controller 205 also generates the cross-sectional image of the three-dimensional image output from the cross-section acquirer 207 as the display image together with the display image in which the information regarding the degree of influence output from the degree-of-influence calculator 103 is superimposed on the fluoroscopic image PI output from the image acquirer 104 and outputs the display image to the display device (not shown), thereby causing the display device (not shown) to display the display image.

Figure 11:
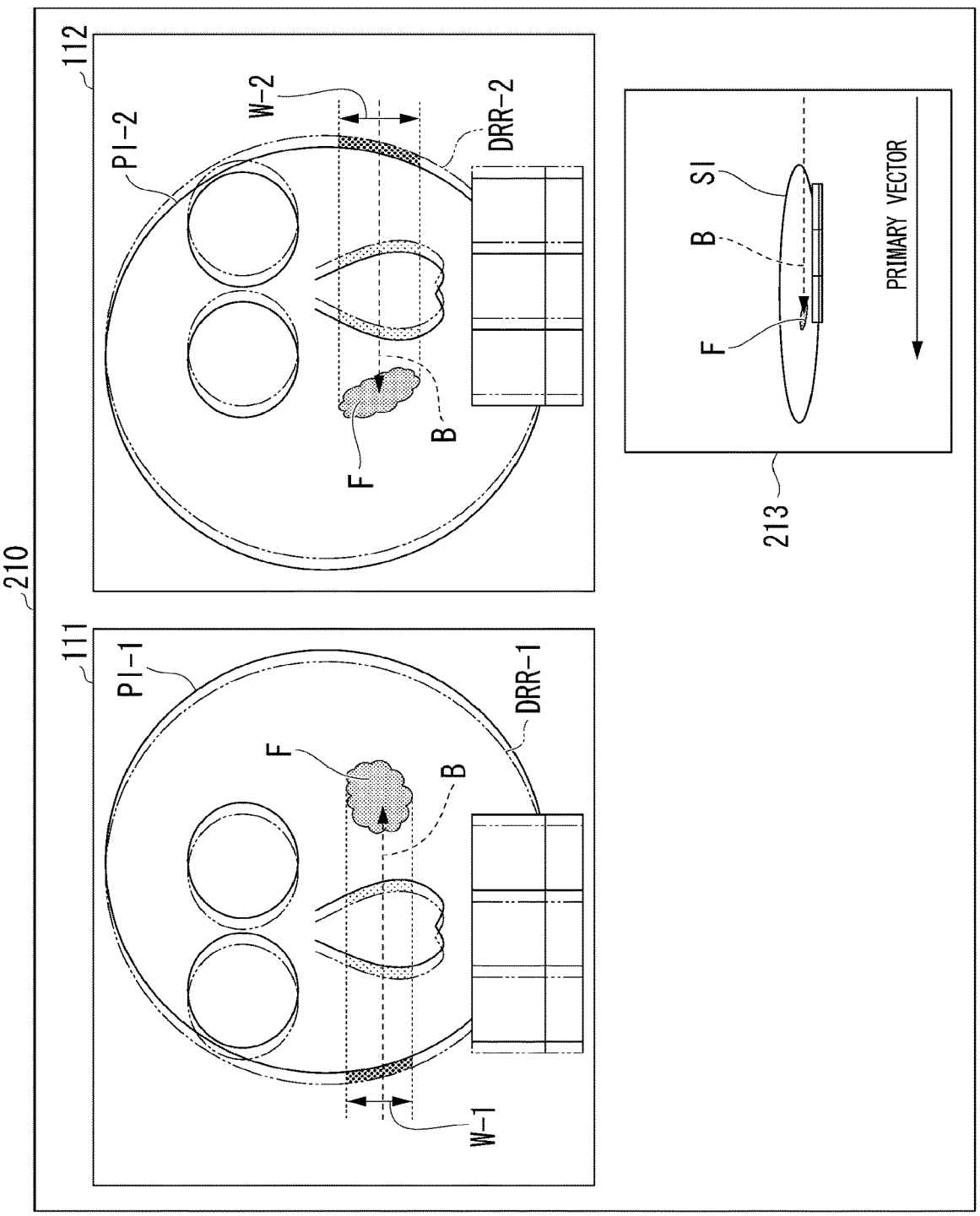
FIG. 11 is a diagram showing an example of a display image generated by a display controller provided in the medical image processing device of the second embodiment.

Here, an example of the display image generated by the display controller 205 will be described. FIG. 11 is a diagram showing an example of a display image generated by the display controller 205 provided in the medical image processing device 200 of the second embodiment. An example of a display image in which a cross-sectional image is displayed together with a composite image of a fluoroscopic image PI and a DRR image on which information regarding the degree of influence is superimposed is shown in FIG. 11.

In FIG. 11, a display image in which information regarding the degree of influence is superimposed on the fluoroscopic image PI captured by the imaging device including each set of the radiation source 12 and the radiation detector 13 provided in the treatment device 10 is shown in the upper part of the display screen 210. Also, in FIG. 11, a display image 213 of the cross-sectional image of the three-dimensional image output from the cross-section acquirer 207 is shown in the lower part of the display screen 210. In the display image 213, the lesion F present within the plane FS is shown in the cross-sectional image SI obtained by segmenting the plane FS set by the cross-section acquirer 207, i.e., in the cross-sectional image ST parallel to the primary vector. Also, in the display image 213, the treatment beam B with which the center of the lesion F is irradiated is shown as an example of the treatment beam B for scanning irradiation on the lesion F. Also, information representing the direction of the primary vector when the display image 213 is projected as the cross-sectional image SI is shown in the display image 213. In the display image 213, an arrow representing the direction of the primary vector is shown as an example of information representing the direction of the primary vector. Also, the display image 213 may be an image in which information regarding the position of the lesion F, the treatment beam B with which the lesion F is irradiated, the direction of the primary vector, and the like is superimposed using the fluoroscopic image PI of the patient P instead of the cross-sectional image SI of the three-dimensional image. Also, the cross-sectional image displayed in the lower part of the display screen 210 is not limited to only the cross-sectional image SI parallel to the primary vector as shown in the display image 213. For example, a display image in which information regarding the position of the lesion F, the treatment beam B with which the lesion F is irradiated, the direction of the primary vector, and the like is superimposed on a plane orthogonal to the cross-sectional image SI shown in the display image 213, i.e., on a cross-sectional image perpendicular to the primary vector, may be shown together with the display image 213 or instead of the display image 213.

Also, the display image 111 and the display image 112 shown in the upper part of the display screen 210 are display images similar to the display screen 110 (see FIG. 5) in the medical image processing device 100 of the first embodiment. In this regard, the irradiation direction of the treatment beam B shown in the display screen 210 is considered for each of the display image 111 and the display image 112. Thus, each of the display image 111 and the display image 112 shown in the upper part of the display screen 210 has a location different from that of the display image 111 or the display image 112 of the display screen 110 in the medical image processing device 100 of the first embodiment shown in FIG. 5.

More specifically, a state in which the treatment beam B is radiated from the right side to the left side is shown in the display image 213 shown in the lower part of the display screen 210. When the irradiation direction of the treatment beam B is considered, a degree of influence associated with pixels (more specifically, pixels of a contour portion of a nose) other than pixels highlighted (conspicuous) in the outermost contour portion irradiated with the treatment beam B within pixels highlighted (conspicuous) in a range (a width) W of the irradiation path of the treatment beam B is thought to be low in the display image 111 and the display image 112 of the display screen 110 in the medical image processing device 100 of the first embodiment shown in FIG. 5. Thus, in each of the display image 111 and the display image 112 shown in the upper part of the display screen 210, a color in which pixels other than those of the outermost contour portion which is irradiated with the treatment beam B within a range (a width) W of the irradiation path of the treatment beam B are colored to be highlighted (conspicuous) is different from a color in which pixels for the outermost contour portion are colored to be highlighted (conspicuous). Also, the difference between the color of highlighted (conspicuous) pixels of the display image 111 and the display image 112 of the display screen 110 in the medical image processing device 100 of the first embodiment shown in FIG. 5 and the color of highlighted (conspicuous) pixels of the display image 111 and the display image 112 shown in the upper part of the display screen 210 is based on the degree of influence calculated by the degree-of-influence calculator 103. Here, the degree-of-influence calculator 103 also calculates the degree of influence on the basis of the treatment plan information output from the treatment plan acquirer 101 in the medical image processing device 100 of the first embodiment. The treatment plan information output from the treatment plan acquirer 101 also includes information regarding the irradiation direction of the treatment beam B in the medical image processing device 100 of the first embodiment. Accordingly, a difference between a color of highlighted (conspicuous) pixels of the display image 111 and the display image 112 of the display screen 110 in the medical image processing device 100 of the first embodiment shown in FIG. 5 and a color of highlighted (conspicuous) pixels of the display image 111 and the display image 112 shown in the upper part of the display screen 210 is not a difference due to the configuration of the medical image processing device 200 because the configuration of the medical image processing device 200 is thought to be similar to that of the medical image processing device 100 of the first embodiment.

The radiation treatment provider (the doctor or the like) using the treatment system 2 performs the patient positioning work while performing comparison (confirmation) with a display image 213 shown in the display screen 210 in addition to the display image 111 and the display image 112 shown in the display screen 210. Thereby, the radiation treatment provider (the doctor or the like) using the treatment system 2 can perform the patient positioning work while easily confirming whether or not there is a location which is likely to have an influence on the effect of the radiation treatment such as a location of bubbles, bone deviation, or the like on a path up to a range in which the treatment beam B reaches the lesion F. At this time, the radiation treatment provider (the doctor or the like) can indicate (input) a location (a specific position) where the position of the patient P deviates on a cross-sectional image SI within the display image 213 shown in the display screen 210 by confirming the display image 111 and the display image 112. Thereby, the cross-section acquirer 207 segments a new cross-sectional image SI by resetting a plane FS in the location indicated (input) by the radiation treatment provider (the doctor or the like) and the display controller 205 causes the display device (not shown) to display the display image 213 of the new cross-sectional image SI. Thereby, the radiation treatment provider (the doctor or the like) can easily confirm a path of the treatment beam B passing through the indicated (input) location from the new display image 213. As a result, the radiation treatment provider (the doctor or the like) can determine whether or not the lesion F within the body of the patient P can be appropriately irradiated with the treatment beam B or the radiation treatment can be performed in a current deviation state of the patient P in the patient positioning work. That is, the radiation treatment provider (the doctor or the like) who is performing the patient positioning work can determine whether or not the patient positioning work has been completed.

Also, in the example of the display image shown in FIG. 11, the display image 213 of the cross-sectional image SI shows the treatment beam B with which the center of the lesion F is irradiated as an example of the treatment beam B subjected to scanning irradiation. However, as shown in the upper part of the example of the display image shown in FIG. 11, a range (a width) W of an irradiation path along which the lesion F is irradiated with the treatment beam B according to scanning irradiation can be obtained from the treatment plan information. Thus, in the medical image processing device 200, the cross-section acquirer 207 assigns information regarding the range (the width) W of the irradiation path capable of being obtained from the treatment plan information to the cross-sectional image SI and outputs the information to the display controller 205. The display controller 205 may be configured to generate the display image 213 representing the range (the width) W of the irradiation path. Also, as described above, when the scanning irradiation is performed with the treatment beam B, the cross-section acquirer 207 sets a plurality of planes FS associated with treatment beams B in irradiation directions. Accordingly, the cross-section acquirer 207 acquires (generates) a plurality of cross-sectional images SI associated with the planes FS. Thus, in the medical image processing device 200, for example, the display controller 205 may be configured to perform switching between display images 213 associated with the plurality of cross-sectional images SI output from the cross-section acquirer 207 in accordance with an instruction of the radiation treatment provider (the doctor or the like). Also, in the medical image processing device 200, for example, the display controller 205 may be configured to show all treatment beams B with which the lesion F is irradiated according to scanning irradiation by combining a plurality of cross-sectional images SI output from the cross-section acquirer 207.

As described above, in the medical image processing device 200 of the second embodiment, as in the medical image processing device 100 of the first embodiment, the treatment plan acquirer 101 also acquires treatment plan information made in the treatment planning stage and the region-of-interest acquirer 102 acquires (extracts) a location where position deviation is large within a region around the irradiation path of the treatment beam B with which the lesion within the body of the patient P is irradiated as the region of interest ROI on the basis of the treatment plan information. Thereby, in the medical image processing device 200 of the second embodiment, as in the medical image processing device 100 of the first embodiment, the degree-of-influence calculator 103 also calculates a degree of influence up to a range when the location (the region of interest ROI) where position deviation is large is irradiated with the treatment beam B within the irradiation path of the treatment beam B with which the lesion within the body of the patient P is irradiated. In the medical image processing device 200 of the second embodiment, as in the medical image processing device 100 of the first embodiment, the display controller 205 generates a display image in which a location where position deviation within the irradiation path of the treatment beam B considered to be important in the patient positioning work is large is highlighted (conspicuous) in accordance with information regarding a degree of influence in the current fluoroscopic image PI of the patient P acquired by the image acquirer 104. Thereby, in the medical image processing device 200 of the second embodiment, as in the medical image processing device 100 of the first embodiment, the radiation treatment provider (the doctor or the like) using the treatment system 2 can perform the patient positioning work while visually and easily confirming deviation between a current position of the patient P and a position of the patient P planned in the treatment planning stage from the display image displayed on the display device (not shown).

Also, in the medical image processing device 200 of the second embodiment, the three-dimensional image acquirer 206 acquires a three-dimensional image captured in the treatment planning stage. In the medical image processing device 200 of the second embodiment, the cross-section acquirer 207 sets a plane along a direction (an angle) of the treatment beam B when a lesion within the body of the patient P or a specific position designated by the radiation treatment provider (the doctor or the like) using the treatment system 2 is irradiated with the treatment beam B and acquires (generates) a cross-sectional image by segmenting the set plane from the three-dimensional space. In the medical image processing device 200 of the second embodiment, the display controller 205 generates a display image of a cross-sectional image. Thereby, in the medical image processing device 200 of the second embodiment, the radiation treatment provider (the doctor or the like) using the treatment system 2 can perform the patient positioning work in consideration of the irradiation direction of the treatment beam B shown in the display image of the cross-sectional image while visually and easily performing comparison (confirmation) with the display image of the cross-sectional image in addition to a display image in which a location where position deviation is large displayed on the display device (not shown) is highlighted (conspicuous). Thereby, the medical image processing device 200 of the second embodiment can more appropriately determine a result of the patient positioning work.

As described above, the medical image processing device 200 further includes the three-dimensional image acquirer 206 configured to acquire a three-dimensional image 3DI obtained by photographing the patient P; and the cross-section acquirer 207 configured to set a plane within a three-dimensional space and acquire a cross-sectional image obtained by segmenting the set plane from the three-dimensional image 3DI. The display controller 205 further generates a display image of the cross-sectional image and causes the display image to be displayed.

Also, as described above, the cross-section acquirer 207 may set the plane according to a primary vector parallel to a passage path of radiation (a treatment beam B) and another vector perpendicular to the primary vector.

Also, as described above, the other vector may be any axial vector (for example, a three-dimensional vector defining the axis Va-1) in the three-dimensional coordinate system (the three-dimensional coordinate system 3DC) predefined in an environment (a treatment room) in which the patient P is irradiated with the treatment beam B.

Also, as described above, the display controller 205 may generate a display image of a cross-sectional image on which information representing the direction of the primary vector is superimposed.

As described above, the medical image processing device of each embodiment sequentially detects deviations between positions of the patient planned at the time of the treatment planning stage and current positions of the patient to be confirmed in the patient positioning work. The medical image processing device of each embodiment sequentially presents information representing the detected position deviations of the patient to the radiation treatment provider (the doctor or the like) using the treatment system. Thereby, in the medical image processing device of each embodiment, the radiation treatment provider (the doctor or the like) can perform patient positioning work so that an error, which is likely to occur in the actual treatment, is reduced while visually and easily confirming the deviation between the position of the patient planned in the treatment planning stage and the current position of the patient. Thereby, the treatment system including the medical image processing device of each embodiment can improve the accuracy of patient positioning. Also, in the treatment system including the medical image processing device of each embodiment, it is possible to shorten a time period required for the patient positioning work and reduce the burden for receiving radiation treatment.

Also, a configuration in which the medical image processing device and the treatment device 10 are separate devices has been described in each embodiment. However, the medical image processing device and the treatment device 10 are not limited to the configuration of separate devices and the medical image processing device and the treatment device 10 may be integrated.

A medical image processing program for use in the treatment system described in the above-described embodiment is a medical image processing program for causing a computer to function as a medical image processing device including: a region-of-interest acquirer configured to acquire a partial region within a body of a patient as a region of interest; a treatment plan acquirer configured to acquire treatment plan information determined in a planning stage of radiation treatment to be performed on the patient; a degree-of-influence calculator configured to calculate a degree of influence representing an influence on the region of interest up to a range until radiation with which the patient is irradiated reaches a target portion to be treated within the body of the patient; and a display controller configured to generate a display image in which information regarding the degree of influence is superimposed on a current fluoroscopic image PI of the patient and cause a display to display the display image.

According to at least one embodiment described above, there are provided a region-of-interest acquirer (102) configured to acquire a partial region within a body of a patient as a region of interest (a region of interest ROI); a treatment plan acquirer (101) configured to acquire treatment plan information determined in a planning stage of radiation treatment to be performed on the patient; a degree-of-influence calculator (103) configured to calculate a degree of influence representing an influence on the region of interest (the region of interest ROI) up to a range until radiation with which the patient is irradiated reaches a target portion (a lesion) to be treated within the body of the patient; and a display controller (105) configured to generate a display image in which information regarding the degree of influence is superimposed on a current fluoroscopic image PI of the patient and cause a display to display the display image, so that a position of the patient can be easily confirmed in patient position alignment work to be performed before radiation treatment is started.

Also, the various functions described above according to the treatment system of each embodiment described above may be performed by recording a program for implementing the functions of the components, which constitute the medical image processing device, such as, for example, the treatment plan acquirer 101, the region-of-interest acquirer 102, the degree-of-influence calculator 103, the image acquirer 104, and the display controller 105 shown in FIG. 2, on a computer-readable recording medium and causing a computer system to read and execute the program recorded on the recording medium. Also, the "computer system" used here may include an operating system (OS) and hardware such as peripheral devices. Also, the "computer system" is assumed to include a homepage providing environment (or displaying environment) when a World Wide Web (WWW) system is used. Also, the "computer-readable recording medium" refers to a storage device such as a flexible disc, a magneto-optical disc, a read-only memory (ROM), a writable non-volatile memory such as a flash memory, a portable medium such as a compact disc-ROM (CD-ROM), and a hard disk embedded in the computer system.

Furthermore, the "computer-readable recording medium" is assumed to include a medium that holds a program for a constant period of time, such as a volatile memory (for example, a dynamic random access memory (DRAM)) inside a computer system serving as a server or a client when the program is transmitted via a network such as the Internet or a communication circuit such as a telephone circuit. Also, the above-described program may be transmitted from a computer system storing the program in a storage device or the like to another computer system via a transmission medium or by transmission waves in a transmission medium. Here, the "transmission medium" for transmitting the program refers to a medium having a function of transmitting information as in a network (a communication network) such as the Internet or a communication circuit (a communication line) such as a telephone circuit. Also, the above-described program may be a program for implementing some of the above-described functions. Further, the above-described program may be a program capable of implementing the above-described function in combination with a program already recorded on the computer system, i.e., a so-called differential file (differential program).

While several embodiments of the present invention have been described, these embodiments have been presented by way of example only, and are not intended to limit the scope of the inventions. These embodiments may be embodied in a variety of other forms. Various omissions, substitutions, and combinations may be made without departing from the spirit of the inventions. The inventions described in the accompanying claims and their equivalents are intended to cover such embodiments or modifications as would fall within the scope and spirit of the inventions.

REFERENCE SIGNS LIST 1, 2 Treatment system
10 Treatment device
11 Treatment table
12, 12-1, 12-2 Radiation source
13, 13-1, 13-2 Radiation detector
14 Treatment beam irradiation gate
100, 200 Medical image processing device
101 Treatment plan acquirer
102 Region-of-interest acquirer
103 Degree-of-influence calculator
104 Image acquirer
105, 205 Display controller
206 Three-dimensional image acquirer
207 Cross-section acquirer

The invention claimed is:

1. A medical image processing device comprising:
circuitry configured to:
    acquire a partial region within a body of a patient as a region of interest;
    acquire treatment plan information determined in a planning stage of radiation treatment to be performed on the patient;
    calculate a degree of influence representing an influence of radiation with which the patient is irradiated on the region of interest up to a range in which the radiation reaches a target portion to be treated within the body of the patient;
    generate a display image in which information regarding the degree of influence is superimposed on a current fluoroscopic image of the patient and cause a display to display the display image;
    calculate the degree of influence on the basis of a degree of overlap between a passage path of the radiation that is radiated and the region of interest; and
    calculate the degree of influence on the basis of a ratio between a volume in which the passage path of the radiation that is radiated overlaps the region of interest and a volume of the region of interest.

2. The medical image processing device according to claim 1,
wherein the circuitry is further configured to acquire locations where deviation between a region of the patient shown in a plan image captured in the planning stage and a corresponding region of the patient shown in the fluoroscopic image is greater than a predetermined threshold value as the region of interest.

3. The medical image processing device according to claim 2,
wherein the circuitry is further configured to acquire a location within a range of the passage path of the radiation among the locations where the deviation is greater than the threshold value as the region of interest.

4. The medical image processing device according to claim 3,
wherein the circuitry is further configured to acquire a location including a predetermined range provided around the range of the passage path of the radiation as the region of interest.

5. The medical image processing device according to claim 1,
wherein the circuitry is further configured to generate the display image in which pixels associated with the region of interest within a range of the passage path of the radiation among pixels of the current fluoroscopic image are highlighted in accordance with the information regarding the degree of influence.

6. The medical image processing device according to claim 5,
wherein the circuitry is further configured to generate the display image in which a color of the pixels to be highlighted is changed.

7. The medical image processing device according to claim 6,
wherein the circuitry is further configured to combine a reconstructed image having a same range as the current fluoroscopic image virtually reconstructed from a plan image captured in the planning stage with the current fluoroscopic image and then to generate the display image in which the pixels to be highlighted are highlighted in accordance with the information regarding the degree of influence.

8. The medical image processing device according to claim 6,
wherein the circuitry is further configured to generate the display image in which pixels within a predetermined range provided around the range of the passage path of the radiation among pixels of the fluoroscopic image are highlighted in a method different from that of the pixels to be highlighted.

9. The medical image processing device according to claim 1, wherein the circuitry is further configured to:
    acquire a three-dimensional image obtained by photographing the patient;
    set a plane within a three-dimensional space and acquire a cross-sectional image obtained by segmenting the set plane from the three-dimensional image; and
    generate a display image of the cross-sectional image and cause the generated display image to be displayed.

10. The medical image processing device according to claim 9,
wherein the circuitry is further configured to set the plane according to a primary vector parallel to the passage path of the radiation and another vector perpendicular to the primary vector.

11. The medical image processing device according to claim 10,
wherein the other vector is one axial direction vector in a three-dimensional coordinate system predefined in an environment where the patient is irradiated with the radiation.

12. The medical image processing device according to claim 10,
wherein the circuitry is further configured to generate the display image of the cross-sectional image on which information representing a direction of the primary vector is superimposed.

13. A treatment system comprising:
the medical image processing device according to claim 1;

a treatment device comprising an irradiator configured to irradiate the target portion to be treated with the radiation and an imaging device configured to capture the fluoroscopic image; and the display configured to display the display image.

14. A medical image processing device comprising:
circuitry configured to:
acquire a partial region within a body of a patient as a region of interest;
acquire treatment plan information determined in a planning stage of radiation treatment to be performed on the patient;
calculate a degree of influence representing an influence of radiation with which the patient is irradiated on the region of interest up to a range in which the radiation reaches a target portion to be treated within the body of the patient;
generate a display image in which information regarding the degree of influence is superimposed on a current fluoroscopic image of the patient and cause a display to display the display image;
calculate the degree of influence on the basis of a degree of overlap between a passage path of the radiation that is radiated and the region of interest; and
calculate the degree of influence on the basis of a shortest distance between the passage path of the radiation that is radiated and the region of interest.

15. A non-transitory computer-readable storage medium storing instructions for causing a computer to:
acquire a partial region within a body of a patient as a region of interest;
acquire treatment plan information determined in a planning stage of radiation treatment to be performed on the patient;
calculate a degree of influence representing an influence of radiation with which the patient is irradiated on the region of interest up to a range in which the radiation reaches a target portion to be treated within the body of the patient;
generate a display image in which information regarding the degree of influence is superimposed on a current fluoroscopic image of the patient and cause a display to display the display image;
calculate the degree of influence on the basis of a degree of overlap between a passage path of the radiation that is radiated and the region of interest; and
calculate the degree of influence on the basis of a ratio between a volume in which the passage path of the radiation that is radiated overlaps the region of interest and a volume of the region of interest.

16. A non-transitory computer-readable storage medium storing instructions for causing a computer to:
acquire a partial region within a body of a patient as a region of interest;
acquire treatment plan information determined in a planning stage of radiation treatment to be performed on the patient;
calculate a degree of influence representing an influence of radiation with which the patient is irradiated on the region of interest up to a range in which the radiation reaches a target portion to be treated within the body of the patient;
generate a display image in which information regarding the degree of influence is superimposed on a current fluoroscopic image of the patient and cause a display to display the display image;
calculate the degree of influence on the basis of a degree of overlap between a passage path of the radiation that is radiated and the region of interest; and
calculate the degree of influence on the basis of a shortest distance between the passage path of the radiation that is radiated and the region of interest.

* * * * *